(12) United States Patent
Dombrowski et al.

(10) Patent No.: US 10,471,244 B2
(45) Date of Patent: Nov. 12, 2019

(54) LIQUID APPLICATOR COMPRISING SINGLE-PIECE BODY

(71) Applicant: 3M INNOVATIVE PROPERTIES COMPANY, St. Paul, MN (US)

(72) Inventors: Alan R. Dombrowski, Woodbury, MN (US); Stephane Levesque, Quebec (CA)

(73) Assignee: 3M Innovative Properties Company, Saint Paul, MN (US)

( * ) Notice: Subject to any disclaimer, the term of this patent is extended or adjusted under 35 U.S.C. 154(b) by 201 days.

(21) Appl. No.: 15/520,089

(22) PCT Filed: Oct. 9, 2015

(86) PCT No.: PCT/US2015/054807
§ 371 (c)(1),
(2) Date: Apr. 19, 2017

(87) PCT Pub. No.: WO2016/064594
PCT Pub. Date: Apr. 28, 2016

(65) Prior Publication Data
US 2017/0304599 A1    Oct. 26, 2017

Related U.S. Application Data

(60) Provisional application No. 62/068,080, filed on Oct. 24, 2014.

(51) Int. Cl.
*B43K 5/14*    (2006.01)
*A61F 13/40*    (2006.01)
(Continued)

(52) U.S. Cl.
CPC ........ *A61M 35/006* (2013.01); *A61M 35/003* (2013.01); *B65D 1/0238* (2013.01); *B65D 1/095* (2013.01)

(58) Field of Classification Search
CPC ... A61M 35/003; A61M 35/006; B65D 1/095; B65D 1/0238
(Continued)

(56) References Cited

U.S. PATENT DOCUMENTS 3,356,244 A    12/1967    Witchell
3,847,151 A    11/1974    D'Alessandro et al.
(Continued)

FOREIGN PATENT DOCUMENTS

CA    2796699    5/2014
EP    0 327 397    8/1989
(Continued)

*Primary Examiner* — Jennifer C Chiang
(74) *Attorney, Agent, or Firm* — 3M Innovative Properties Company; Trisha D. Adamson

(57) ABSTRACT

A liquid applicator comprising an absorbent member, and a single-piece, unitary body. The body can include a closed container defining a reservoir, and a tab. The container can include a main portion, a transition portion, a rib, and a chamber located in the tab and coupled to the transition portion via a frangible connection. The main portion, the transition portion, the rib, and the chamber can each define a portion of the reservoir, and at least the main portion, the transition portion, and the rib can have a uniform wall thickness. The tab can include the chamber and can be coupled to the transition portion at least by the frangible connection, the tab being movable with respect to the transition portion between a first position in which the frangible connection is intact and a second position in which the frangible connection is fractured.

18 Claims, 6 Drawing Sheets

(51) Int. Cl.
*A61M 35/00* (2006.01)
*B65D 1/02* (2006.01)
*B65D 1/09* (2006.01)

(58) Field of Classification Search
USPC .................................................. 401/132, 133
See application file for complete search history.

(56) References Cited

U.S. PATENT DOCUMENTS

| | | |
|---|---|---|
| 3,917,120 A | 11/1975 | Larenz |
| D245,221 S | 8/1977 | Hoyt |
| 4,248,227 A | 2/1981 | Thomas |
| D289,200 S | 4/1987 | Newell |
| 4,671,763 A | 6/1987 | Weiler |
| 4,979,630 A | 12/1990 | Rose |
| 4,995,519 A | 2/1991 | Rose |
| 5,229,061 A | 7/1993 | Van Dyke |
| D347,277 S | 5/1994 | Snedden |
| 5,326,603 A | 7/1994 | Van Dyke |
| D358,466 S | 5/1995 | Harris |
| D362,304 S | 9/1995 | Wilson |
| 5,658,084 A | 8/1997 | Wirt |
| 5,908,124 A | 6/1999 | Klauke |
| D425,617 S | 5/2000 | Snedden |
| 6,068,148 A | 5/2000 | Weiler |
| 6,516,947 B1 | 2/2003 | Van Dyke |
| 6,536,975 B1 | 3/2003 | Tufts |
| 6,846,459 B2 | 1/2005 | Snedden |
| 6,869,242 B2 | 3/2005 | May |
| 7,028,862 B2 | 4/2006 | Poynter |
| D532,295 S | 11/2006 | Stull |
| 7,182,536 B2 | 2/2007 | Tufts |
| 7,188,750 B2 | 3/2007 | Vogel |
| D551,760 S | 9/2007 | Zahn |
| D565,193 S | 3/2008 | Price |
| 7,540,389 B2 | 6/2009 | Fontana |
| 7,614,811 B2 | 11/2009 | Kaufman |
| 7,757,852 B2 | 7/2010 | Fontana |
| 7,866,514 B1 | 1/2011 | Hansen |
| 7,946,779 B2 | 5/2011 | Kaufman |
| 7,976,234 B2 | 7/2011 | May |
| 8,083,425 B2 | 12/2011 | Kaufman |
| 8,105,306 B2 | 1/2012 | Davis |
| 8,186,897 B2 * | 5/2012 | Kaufman ............. A45D 34/042 401/133 |
| 8,215,859 B2 | 7/2012 | Kaufman |
| 8,377,029 B2 | 2/2013 | Nagao |
| 9,867,973 B2 * | 1/2018 | Chiang ............... A61M 35/006 |
| 2004/0253039 A1 | 12/2004 | Stenton |
| 2006/0108385 A1 | 5/2006 | Zahn |
| 2011/0031157 A1 | 2/2011 | Nakano |
| 2011/0142527 A1 | 6/2011 | Kaufman |
| 2011/0248045 A1 | 10/2011 | Harris |
| 2011/0315720 A1 | 12/2011 | Marshall |
| 2012/0051829 A1 | 3/2012 | Margoosian |
| 2012/0230753 A1 | 9/2012 | Kaufman |
| 2013/0015204 A1 | 1/2013 | Gol |
| 2014/0126949 A1 | 5/2014 | Kaufman |
| 2014/0371694 A1 | 12/2014 | Chiang |

FOREIGN PATENT DOCUMENTS

| | | |
|---|---|---|
| GB | 2 185 880 | 8/1987 |
| GB | 8 802 349 | 3/1988 |
| JP | 2011-37038 | 2/2011 |

* cited by examiner

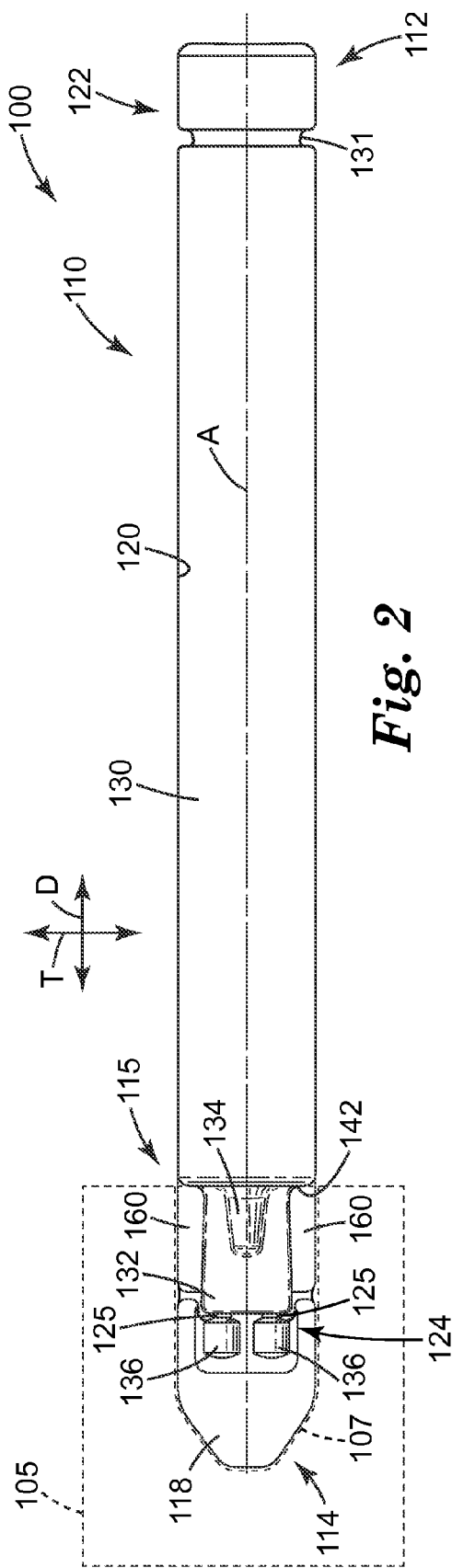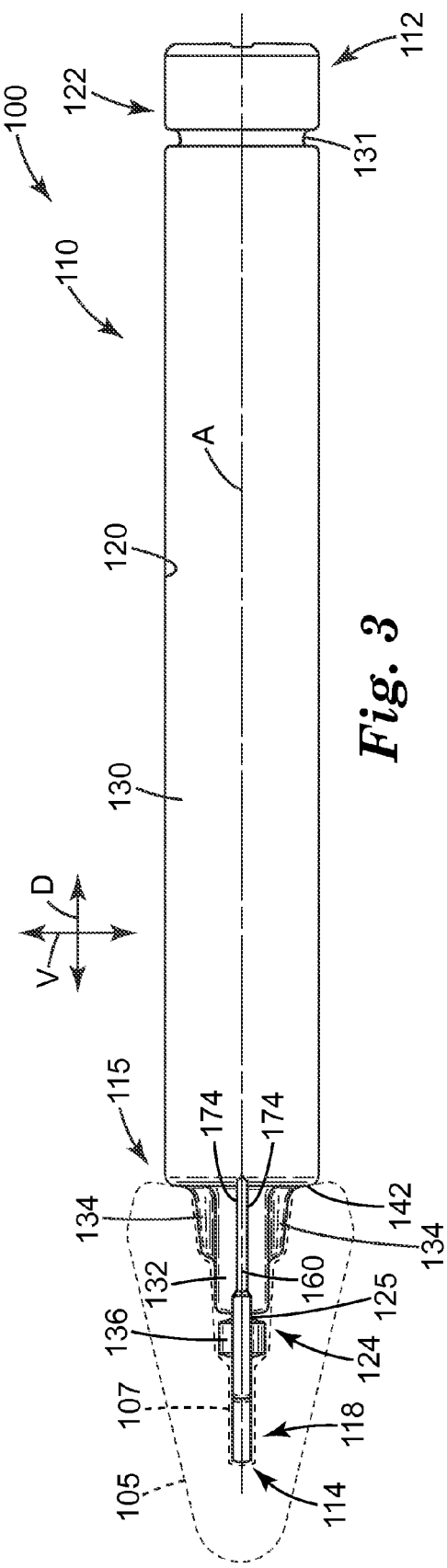

LIQUID APPLICATOR COMPRISING SINGLE-PIECE BODY

CROSS REFERENCE TO RELATED APPLICATIONS

This application is a national stage filing under 35 U.S.C. 371 of PCT/US2015/054807, filed Oct. 9, 2015, which claims the benefit of U.S. Provisional Patent Application No. 62/068,080, filed Oct. 24, 2014, the disclosure of which is incorporated by reference in their entirety herein.

FIELD

The present disclosure generally relates to liquid applicators for applying a liquid to a surface, such applicators having particular utility in the field of antiseptic skin surface preparation. More particularly, the present disclosure generally relates to liquid applicators useful in applying pre-operative surgical scrubs or paints to skin.

BACKGROUND

Antiseptic preparation of patient's skin for surgery conventionally includes a 30 second to a 2 minute scrubbing of the affected area with an antiseptic solution. Devices have been developed in an attempt to prevent solution dripping associated with these techniques, and to reduce the time required for application of the antiseptic solution.

Some existing liquid applicators house the liquid in a glass ampoule which is then crushed to activate the device and saturate the sponge. For example, Wirt (U.S. Pat. No. 5,658,084) and Tufts (U.S. Pat. No. 6,536,975) disclose two different ways to rupture/break a glass ampoule in order to activate an applicator. Glass ampoules are common, because glass is impermeable to ethylene oxide (EO), which is often used during a sterilization process for sterilizing applicators. Wirt and Tufts also disclose applicators comprising numerous parts, including parts for preventing glass shards from reaching a patient during the application process. The applicator bodies are rigid, allowing the antiseptic to freely flow (i.e., in an uncontrolled manner) to a sponge after activation and before application to a target surface.

As an alternate approach to using glass ampoules, applicators using plastic bodies with frangible plastic tips have been developed. In such constructions, the applicator body also functions as a container for the solution, eliminating the glass ampoule. These applicators consist of an applicator handle comprising the solution, a frangible tip, and an end cap that closes the applicator handle, opposite the tip. The tip is flexed or twisted to break off a weakened tip region. Such applicators are often complex to construct, and are formed of multiple assembly components.

For example, Kaufman (U.S. Pat. No. 7,614,811) and Margoosian (U.S. Publication No. 2012/0051829) both disclose plastic applicators made of multiple plastic components with frangible plastic tips and squeezable applicator handles. However, these applicators are difficult and costly to assemble, and have multiple weld seams and joints that are susceptible to failure. Kaufman (U.S. Publication No. 2014/0126949) discloses an applicator where the frangible tip and the container body are integrated into a single piece, manufactured using an injection molding process. However, the resulting single piece includes an open end that still requires a secondary capping operation, adding another component and increasing assembly cost.

Van Dyke (U.S. Pat. No. 5,229,061) discloses a dip molding process for producing a dispensing container that has a frangible portion that is broken away during use. The resulting molded dispensing container still has an open end which needs to be sealed or have a secondary end cap attached when the applicator is filled. This dip molding process uses a core or a mold in order to form the internal geometry, including the break region.

Weiler (U.S. Pat. No. 4,671,763) and Poynter (U.S. Pat. No. 7,028,862) are two examples of containers formed by a blow-fill-seal (BFS) process. Poynter discloses a removable cap, a frangible break line, and a cap chamber. When the removable cap is grasped and twisted, the frangible break line is fractured, and the removable cap is removed, allowing the contents of the container to be expelled.

D'Alessandro (U.S. Pat. No. 3,847,151) teaches a liquid dispensing device for antiseptically cleansing a surface. This device has a hollow handle, and a nozzle with a stress raiser so that the end portion of the nozzle may be ruptured, and a surrounding web. The device allows for a portion of the web to be bent or flexed (e.g., to 45 degrees) after rupturing the end of the nozzle to allow the handle and a user's hand to be kept away from the surface to be cleaned. However, such a stepwise fracturing and bending process can be unnecessarily and ergonomically cumbersome.

Margoosian (CA Patent No. 2796699) discloses a container body that can be formed by a BFS method. However, this container body is only a portion of a multi-component liquid dispensing applicator, requiring multiple assembly steps.

In summary, existing applicators are often difficult and costly to assemble, requiring numerous separate components, and include multiple weld seams and joints susceptible to failure.

SUMMARY

Based on the limitations described above with existing applicators, there remains a need for a liquid applicator comprising a minimum number of parts, and a method of manufacturing the applicator, that reduces the cost of the finished product, while maintaining key features necessary to provide a controlled flow liquid applicator with a facile activation mechanism.

Some aspects of the present disclosure provide a liquid applicator. The applicator can include an absorbent member configured to dispense a liquid composition, and a single-piece, unitary body having a central longitudinal axis that defines a longitudinal direction. The body can further have a lateral direction oriented substantially perpendicularly with respect to the longitudinal direction and a vertical direction oriented substantially perpendicularly with respect to the longitudinal direction and the lateral direction. The body can be configured to be coupled to the absorbent member and can provide at least one coupling surface for the absorbent member. The body can include a closed container defining a reservoir, wherein the liquid composition is positioned in at least a portion of the reservoir, wherein the container includes a closed proximal end and a closed distal end and is configured to be changed from a closed state in which the reservoir is not in fluid communication with ambience to an open state in which the reservoir is in fluid communication with ambience. The container can further include a main portion defining the closed proximal end of the container and including a distal end; a transition portion extending distally from the distal end of the main portion, the transition portion having a cross-sectional area less than the cross-sectional area of the main portion, the transition portion having a length in the longitudinal direction, the transition portion configured to be coupled to the absorbent member; a rib extending longitudinally adjacent the transition portion from the distal end of the main portion to a location along the length of the transition portion, the rib having a vertical height that extends vertically from an outer surface of the transition portion; and a chamber defining the closed distal end of the container, the chamber coupled to the transition portion via a frangible connection, such that the container is in the closed state when the frangible connection is intact and the container is in the open state and in fluid communication with ambience via an aperture formed in the transition portion when the frangible connection is fractured; wherein the main portion, the transition portion, the rib, and the chamber each define a portion of the reservoir, and wherein at least the main portion, the transition portion, and the rib have a uniform wall thickness. The body can further include a tab comprising the chamber and being coupled to the transition portion at least by the frangible connection, the tab being movable with respect to the transition portion between a first position in which the frangible connection is intact and a second position in which the frangible connection is fractured.

Other features and aspects of the present disclosure will become apparent by consideration of the detailed description and accompanying drawings.

BRIEF DESCRIPTION OF THE DRAWINGS

FIG. 2 is a top plan view of the liquid applicator of FIG. 1.

FIG. 3 is a side elevational view of the liquid applicator of FIGS. 1 and 2.

DETAILED DESCRIPTION

Figure 1:
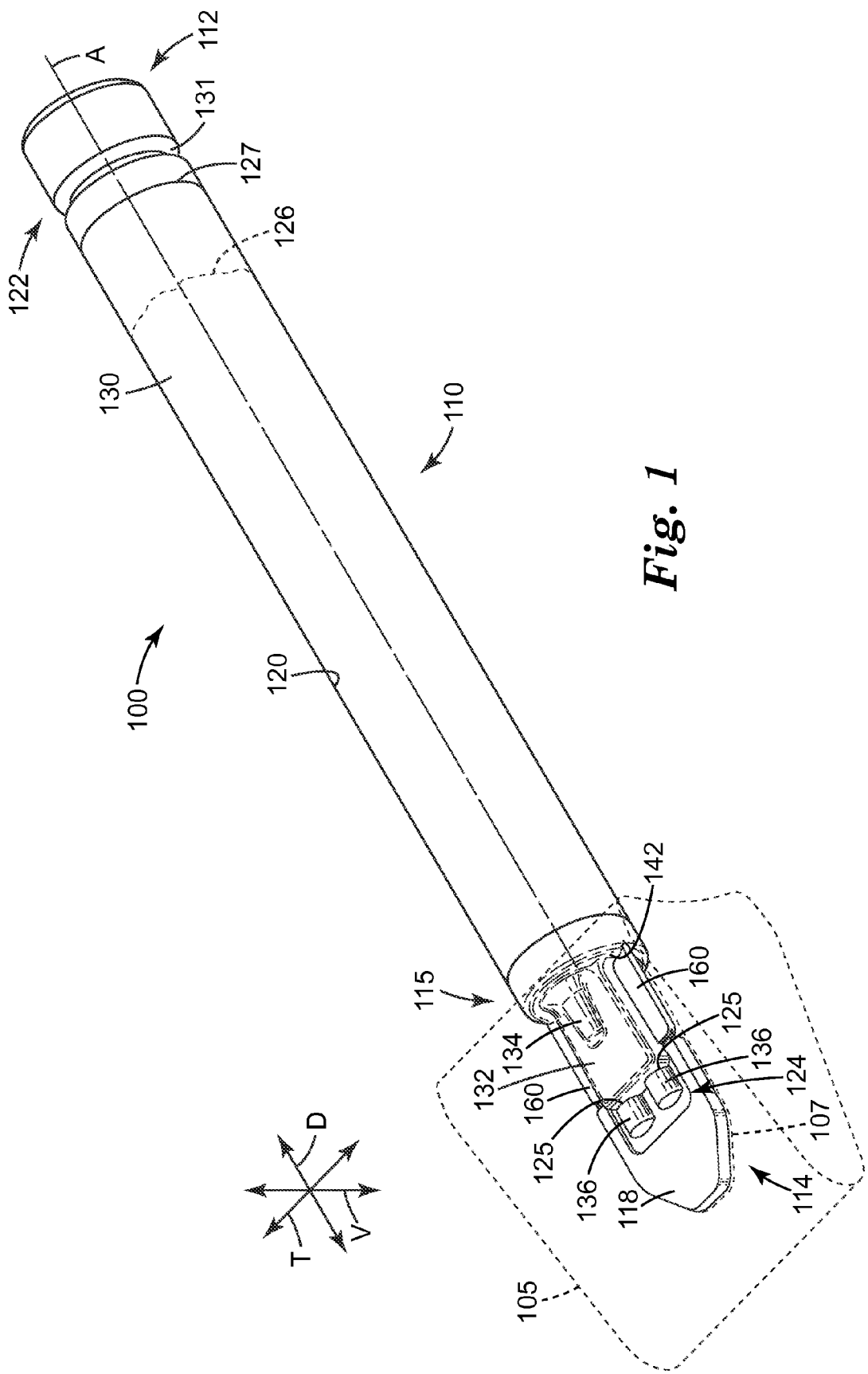
FIG. 1 is a top perspective view of a liquid applicator according to one embodiment of the present disclosure.

The present disclosure generally relates to liquid applicators having particular utility in the field of antiseptic skin surface preparation, such as in the application of pre-operative surgical scrubs or paints to skin. The applicators of the present disclosure generally include (i) an absorbent member configured to absorb a liquid composition of interest and apply that liquid composition to a surface; and (ii) a single-piece, unitary, integral body that contains the liquid composition in a closed container and is configured to be coupled to the absorbent member. The closed container is configured to be opened by fracturing a portion of the body (e.g., during, or just prior to, use) and thereby opening the container, placing the interior reservoir of the container (and the liquid composition) in fluid communication with ambience (and the absorbent member, when coupled to the body). The single, unitary body of applicators of the present disclosure provide a facile and reliable activation mechanism, liquid flow control, and one or more coupling surfaces for the absorbent member.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," and "having," and variations thereof, are meant to encompass the items listed thereafter, and equivalents thereof, as well as additional items.

Unless specified or limited otherwise, the terms "supported," and "coupled" and variations thereof are used broadly and encompass both direct and indirect supports and couplings.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The terms "room temperature" and "ambient temperature" are used interchangeably to mean a temperature in the range of 20° C. to 25° C.

The phase "substantially transparent" is generally used to refer to a body or substrate that transmits at least 50% of electromagnetic radiation having wavelengths at a selected wavelength or within a selected range of wavelengths in the ultraviolet to infrared spectrum (e.g., from about 200 nm to about 1400 nm; "UV-IR"), in some embodiments, at least about 75% of a selected wavelength (or range) in the UV-IR spectrum, and in some embodiments, at least about 90% of a selected wavelength (or range) in the UV-IR spectrum.

The phrase "substantially non-transparent" is generally used to refer to a body or substrate that transmits less than 50% of electromagnetic radiation having wavelengths at a selected wavelength or within a selected range of wavelengths in the ultraviolet to infrared spectrum (e.g., from about 200 nm to about 1400 nm; "UV-IR"), in some embodiments, less than 25% of a selected wavelength (or range) in the UV-IR spectrum, and in some embodiments, less than 10% of a selected wavelength (or range) in the UV-IR spectrum.

The terms "longitudinal" and "axial" are used to refer to a direction or axis that is generally parallel to a central longitudinal axis of an applicator and generally parallel to the overall direction of liquid flow.

The terms "lateral" and "transverse" are used to refer to a direction or axis that is perpendicular to the central longitudinal axis the longitudinal direction.

The terms "vertical" and "normal" are used to refer to a direction or axis that is normal to both the longitudinal and lateral directions (or axes).

The phrase "horizontal surface" is used to refer to a surface that extends in, or has dimensions in the longitudinal and lateral directions and is oriented substantially perpendicularly with respect to the vertical direction. A horizontal surface can include a substantially horizontal surface that predominantly extends in the longitudinal and lateral dimensions but may have a small vertical dimension, relative to its lateral and longitudinal dimensions. For example, in some embodiments, a substantially horizontal surface can have a vertical dimension that is no greater than 10% of its longitudinal or lateral dimension, in some embodiments, no greater than 5%, in some embodiments, no greater than 2%, and in some embodiments, no greater than 1%.

The phrase "vertical surface" is used to refer to a surface that extends in, or has dimensions in the vertical and lateral directions and is oriented substantially perpendicularly with respect to the longitudinal direction. A vertical surface can include a substantially vertical surface that predominantly extends in the vertical and lateral dimensions but may have a small longitudinal dimension, relative to its vertical and lateral dimensions. For example, in some embodiments, a substantially vertical surface can have a longitudinal dimension that is no greater than 10% of its vertical or lateral dimension, in some embodiments, no greater than 5%, in some embodiments, no greater than 2%, and in some embodiments, no greater than 1%.

The phrase "profile surface" is used to refer to a surface that extends in, or has dimensions in the vertical and longitudinal directions and is oriented substantially perpendicularly with respect to the lateral direction. A profile surface can include a substantially profile surface that predominantly extends in the vertical and longitudinal dimensions but may have a small lateral dimension, relative to its vertical and longitudinal dimensions. For example, in some embodiments, a substantially profile surface can have a lateral dimension that is no greater than 10% of its vertical or longitudinal dimension, in some embodiments, no greater than 5%, in some embodiments, no greater than 2%, and in some embodiments, no greater than 1%.

The term "proximal" and "distal" are used to represent longitudinal or axial directions, relative to a user (e.g., a medical practitioner) using or holding the applicator. That is, the term "distal" is used to refer to the direction away from the medical practitioner (and toward a surface (e.g., a skin surface) to be treated, i.e., to which the applicator will apply a liquid); and the term "proximal" is used to refer to the direction toward the user (and away from the surface to be treated). For example, the distal end of an applicator is configured to be directed toward, or even pressed against, the surface to be treated, while the proximal end extends away from the surface and toward the user. Similarly, the distal end of any portion or component of an applicator is configured to be directed or oriented toward the surface to be treated and is oriented toward the distal end of the applicator or forms or defines the distal end of the applicator. In addition, the proximal end of any portion or component of an applicator is configured to be directed or oriented away from the surface to be treated and is oriented toward the proximal end of the applicator or forms or defines the proximal end of the applicator.

The phrase "uniform wall thickness" or "the same wall thickness" is used to describe various portions of the applicators of the present disclosure as having the same nominal (or target) wall thickness, within normal deviations and variations that may occur in a typical blow-fill-seal (BFS) process. For example, in some embodiments, various portions of the applicator can be referred to as having a "uniform wall thickness" if the thicknesses of the portions vary by no more than ±10%; in some embodiments, by no more than ±8%; in some embodiments, by no more than ±5%; in some embodiments, by no more than ±3%; in some embodiments, by no more than ±2%; and in some embodiments, by no more than ±1%.

The applicators of the present disclosure represent a significant reduction in part numbers and can greatly simplify the assembly or fabrication process by eliminating the need for a secondary filling or assembly step. In addition, the applicators of the present disclosure can be formed by a process that includes aseptic or sterile filling of the liquid composition.

In addition, because the body of the applicator is single-piece, unitary, and integral, the body does not include any seams, seals, or joints that result from coupling multiple parts together and that are susceptible to failure and could potentially be the source of leaks (e.g., during storage or use).

Applicators of the present disclosure generally have sufficient strength and rigidity at the distal end to enable fracturing the body (and opening the container containing the liquid) at the desired location and under the desired force, and applying a force to apply a liquid during use without the applicator kinking or buckling, while also providing sufficient flexibility at or toward the proximal end to enable squeezing or pumping the container to control the flow of liquid out of the container. Forming an applicator of a single-piece, unitary body that possessed this balance of material properties presented unique challenges that the present inventors overcame.

The single-piece unitary body of applicators of the present disclosure can be formed by a variety of processes and particularly can be formed by blow-fill-seal (BFS) processes, in which the resulting body has the desired shape, configuration and structural properties, and contains the liquid composition. Such BFS processes can be fully automated and can include sterile filling of the liquid composition, such that a single process can be used to form, fill and seal the applicator.

Blow-Fill-Seal (BFS) is a manufacturing process where a container system is molded and filled at the same time. Blow Fill Seal uses a combination of negative and positive pressure (i.e., vacuum and blow molding) to form the geometry of a part without any internal mold cores, along with aseptic liquid filling to fill the part with a sterile liquid composition. BFS containers eliminate the need for container caps or closures, since the finished product is one unitary part with an integrated closure system. Thus, BFS containers result in significant cost reductions due to the elimination of secondary assembly processing (e.g., filling and closing). The present inventors recognized that a liquid applicator that could be manufactured using a BFS process could result in significant cost savings due to the integration of multiple components into a single body. However, significant design challenges had to be overcome in order meet the above-described combination of features and material properties in a single BFS body.

Figure 5:
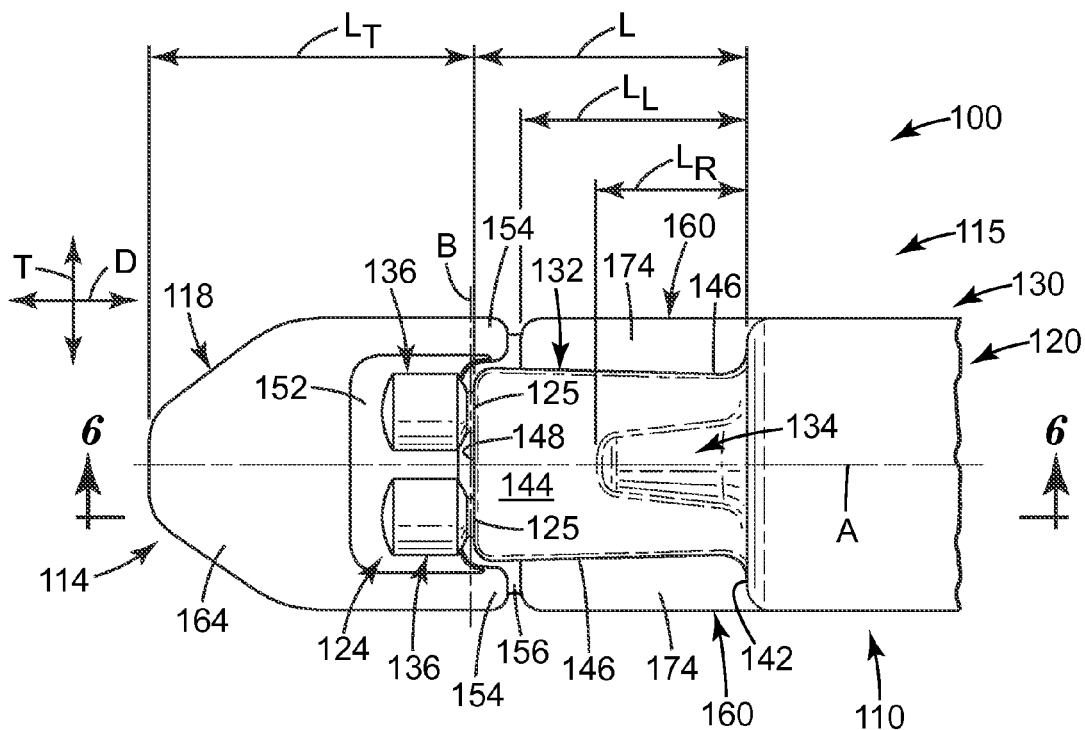
FIG. 5 is a close-up top plan view of the distal end of the liquid applicator of FIGS. 1-4.
Figure 6:
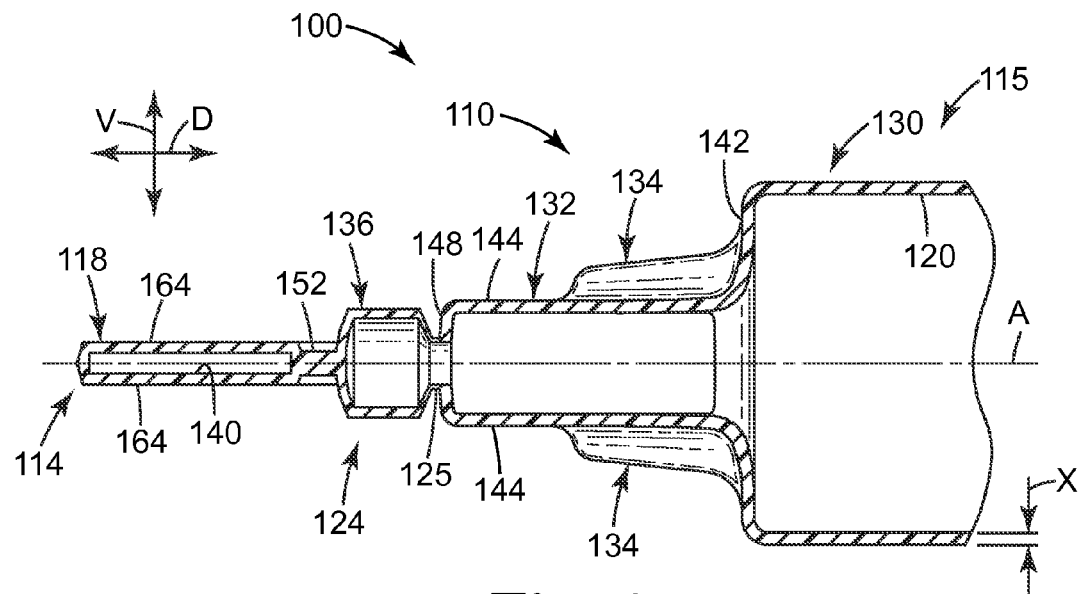
FIG. 6 is a close-up side cross-sectional view of the distal end of the liquid applicator of FIGS. 1-5.
Figure 7A:
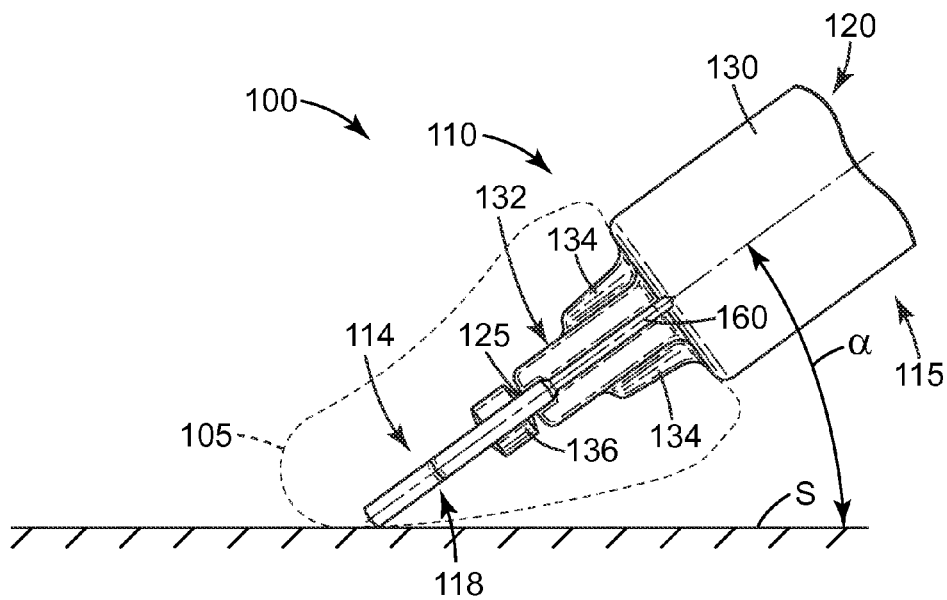
FIGS. 7A-7C illustrate a method of using the liquid applicator of FIGS. 1-6.
Figure 7B:
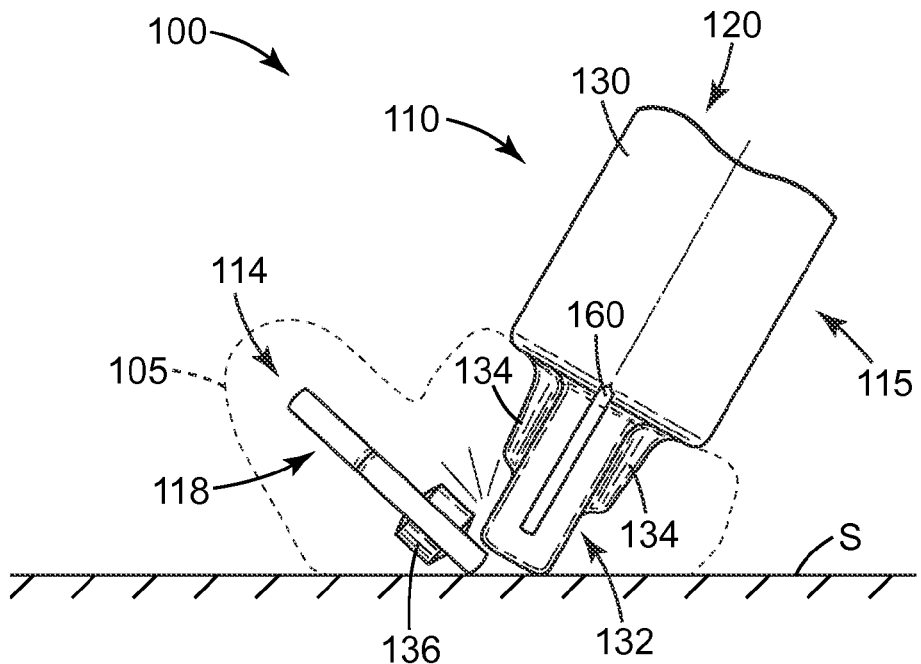
Figure 7C:
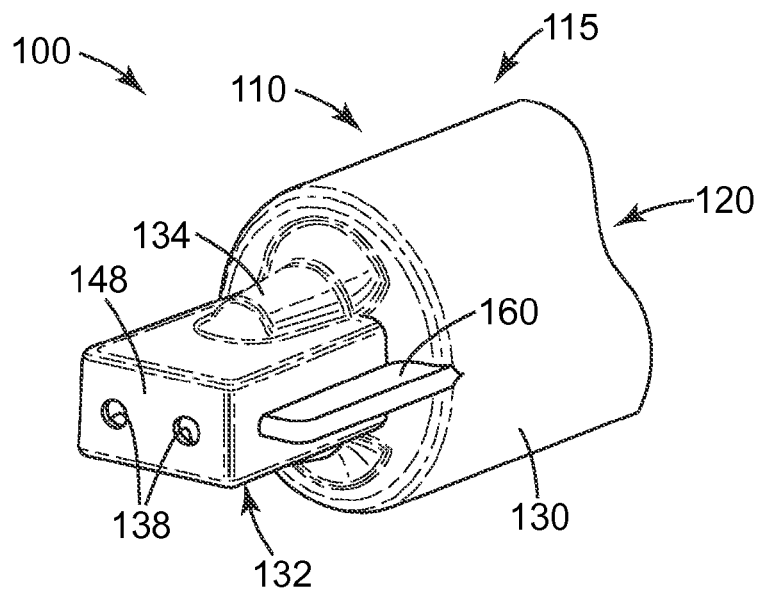

FIGS. 1-6 illustrate a liquid applicator 100 according to one embodiment of the present disclosure, and FIGS. 7A-7C illustrate a method of using the liquid applicator 100.

As shown in FIGS. 1-3, the applicator 100 can include an absorbent member 105, a single-piece, unitary, integral body 110, and a central longitudinal axis A that defines a longitudinal direction D. The applicator 100 further includes a lateral (or transverse) direction T oriented substantially perpendicularly with respect to the central longitudinal axis A and the longitudinal direction D, and a vertical (or normal) direction V oriented substantially perpendicularly with respect to the longitudinal direction D (and the central longitudinal axis A) and the lateral direction T. The central longitudinal axis A, the longitudinal direction D, the lateral direction T, and the vertical direction V can be referred to as representing an axis and directions, respectively, of the body 110 or of the applicator 100 as a whole.

In some embodiments, the applicator 100 (i.e., the body 110) can have at least one plane of symmetry. For example, as shown in FIGS. 3, 6 and 7A-7C, in some embodiments, the applicator 100 can be symmetrical about a horizontal cross-section that is taken at a vertical center of the applicator 100, such that a top vertical half of the applicator 100 is symmetrical with a bottom vertical half of the applicator 100. As further shown, in some embodiments, the applicator 100 can be symmetrical about a vertical cross-section that is taken at a lateral center (i.e., at the central longitudinal axis A) of the applicator 100, such that a first (left) lateral half of the applicator 100 is symmetrical with a second (right) lateral half of the applicator 100.

The body 110 can include a container 115 that defines a reservoir 120, and a tab 118, which is described in greater detail below. The container 115 can form or define at least a portion of a proximal end 112 of the body 110, and the tab 118 can form or define at least a portion of a distal end 114 of the body 110.

The container 115 is illustrated in FIGS. 1-6 as being closed or in a closed state and including a first closed proximal end 122 and a second closed distal end 124. In the closed state, the reservoir 120 is not in fluid communication with ambience (or the absorbent member 105, when the absorbent member 105 and the body 110 are coupled together). A liquid composition 126 (see FIG. 1) can be positioned in at least a portion of the reservoir 120, and need not completely fill the reservoir 120. While illustrated in FIGS. 1-6 in a first closed state, the container 115 is configured to be changed to a second open state (as shown in FIG. 7B and discussed below) in which the reservoir 120 is in fluid communication with ambience (and the absorbent member 105, when the absorbent member 105 and the body 110 are coupled together) to deliver and apply the liquid composition to a desired surface (e.g., a patient's skin surface). As described in greater detail below, the tab 118 is coupled to the container 115 via at least one frangible connection 125 (two are shown in the embodiment illustrated in FIGS. 1-7C), and the tab 118 is movable between a first position in which the frangible connection is intact and the container 115 is in the closed state, and a second position in which the frangible connection is fractured and the container 115 is in the open state.

The container 115 can include or be defined by at least a main portion (or handle) 130, a transition portion 132, one or more ribs 134, and one or more chambers (or bubbles, capsules, blisters, or cells) 136 (two are shown in the embodiment illustrated in FIGS. 1-7C). The main portion 130, the transition portion 132, the one or more ribs 134, and the one or more chambers 136 can each define a portion of the reservoir 120. As shown in FIGS. 1-3, the main portion 130 of the container 115 can include or define the closed proximal end 122 of the container 115, and as shown in FIGS. 1-6, the one or more chambers 136 can include or define the closed distal end 124 of the container 115.

In some embodiments, the absorbent member 105 can include a recess (e.g., a slot) 107 dimensioned to receive at least a portion of the body 110, e.g., at least the distal end 114 of the body 110. In some embodiments, the recess 107 can be dimensioned to receive at least a portion of one or more of the tab 118, the chamber(s) 136, the transition portion 132, and the rib(s) 134. In some embodiments, the absorbent member 105 can be sized to be at least slightly smaller than the volume of the portion of the body 110 to be received in the absorbent member 105, and the slot 107 can be increased or stretched in response to coupling the body 110 to the absorbent member 105 (e.g., in response to inserting the body 110 in the slot 107).

The absorbent member 105 and the body 110 can be coupled together via any of a variety of coupling means, including, but not limited to, adhesives, cohesives, welding (e.g., sonic (e.g., ultrasonic) welding, radio-frequency (RF) welding, hot plate welding), any thermal bonding technique (e.g., heat and/or pressure applied to one or both of the components to be coupled), other suitable coupling means, or combinations thereof. In some embodiments, it can be advantageous for the absorbent member 105 to be semi-permanently or permanently coupled to the body 110, such that the absorbent member 105 and the body 110 are not easily decoupled, e.g., during use. Semi-permanent or permanent coupling generally refers to coupling that cannot be undone (decoupled) without causing some damage to one or both of the elements coupled together.

As mentioned above, the one or more chambers 136 can form a portion of the container 115 and define the closed distal end 124 of the container 115. As shown, the chamber(s) 136 are coupled to the remainder of the container 115, e.g., the transition portion 132, via the frangible connection(s) 125. As further shown, the tab 118 can include the chamber(s) 136, such that the chamber(s) 136 are movable with the tab 118 between the first and second positions. When the frangible connection(s) 125 are fractured, the small channel(s) fluidly connecting the chamber(s) 136 with the remainder of the container 115 are broken, such that one or more aperture(s) 138 (see FIG. 7C) are formed (e.g., in the transition portion 132), and the container 115 is changed to its open state. In the open state, the reservoir 120 is in fluid communication with ambience, and the liquid composition 126 can be moved out of the reservoir 120. The fracturing of the frangible connection(s) 125 and changing of the container 115 from the closed state to the open state can be referred to as "activation" of the applicator 100.

In some embodiments, the tab 118 can pivot or rotate relative to the rest of the body 110 (e.g., the transition portion 132 and the main portion 130) about a transverse axis B (see FIG. 5) that passes through the frangible connection(s) 125, e.g., through the vertical center of the frangible connection(s) 125. As shown in FIG. 5, the transverse axis B is oriented substantially along the lateral direction T and substantially perpendicularly with respect to the longitudinal direction D (and the central longitudinal axis A, as well as the vertical direction V). In such embodiments, the tab 118 can move between the first position and the second position by pivoting about the transverse axis B (i.e., to change the container 115 from the closed state to the open state by fracturing the frangible connection(s) 125). In such embodiments, the applicator 100 can be referred to as a "press-to-activate" applicator 100, and such activation can be done manually or by pressing the tab 118 (i.e., a distal end thereof) against a surface, e.g., a hard surface. Such activation is described in greater detail below with respect to FIGS. 7A-7C. In some press-to-activate embodiments, the tab 118 may be pressed back and forth one or more times to fracture the frangible connections 125.

In some press-to-activate embodiments, when the tab 118 is in the first position (and the container 115 is in the closed state), the tab 118 can be oriented substantially horizontally, and aligned with the longitudinal direction D (and, in some embodiments, the central longitudinal axis A), such that the tab 118 has top and bottom substantially horizontal surfaces, and the frangible connection(s) 125 are intact. When the tab 118 is in the second position (and the container 115 is in the open state), the tab 118 can be moved out of alignment with the longitudinal direction D to be oriented at an angle (i.e., a non-zero angle) with respect to the longitudinal direction D.

In some embodiments, when the tab 118 is in the second position, the tab 118 can be oriented at an angle of no greater than 135 degrees with respect to the longitudinal direction D. That is, in some embodiments employing press-to-activate, the tab 118 need not rotate more than 135 degrees with respect to the longitudinal direction D in order to fracture the frangible connection(s) 125. In some embodiments, when the tab 118 is in the second position, the tab 118 can be oriented at an angle of no greater than 120 degrees; in some embodiments, no greater than 90 degrees; in some embodiments, no greater than 60 degrees; and in some embodiments, no greater than 45 degrees. In some embodiments, the tab 118 can be rotated to an angle at which the chamber(s) 136 (e.g., a side thereof) press against the transition portion 132 (e.g., a distal end 148 thereof), using that contact between the chamber(s) 136 and the transition portion 132 as leverage to further fracture the frangible connection(s) 125 (e.g., a bottom thereof) in a tensile mode. In some embodiments, the larger angles may be necessary, e.g., to provide a sufficient elongation of the frangible connection(s) 125 to cause fracture.

The material makeup of the body 110, as well as the wall thickness of the body 110, can be controlled (along with other factors, such as the length of the transition portion 132, and the configuration of the rib 134) to determine at what applied force and at what angle the frangible connection(s) 125 fracture. The configuration (e.g., material thickness) of the frangible connection(s) 125 can also have affect the activation force, i.e., the thinner the frangible connection (s) 125 are, the easier they will fracture under lower applied forces. The length of the tab 118 in the longitudinal direction D, as discussed in greater detail below, can also add a mechanical advantage to press the applicator on a solid surface and transfer the force to the frangible connection(s) 125. In some press-to-activate embodiments, the tab 118 can be positioned about at a vertical center of the applicator 100 (and the body 110), such that the tab 118 is oriented along the central longitudinal axis A when in its first position, as shown in FIGS. 3, 6 and 7A.

In some embodiments, the tab 118 (and the chamber(s) 136) can be rotated (i.e., twisted) about the longitudinal direction D (e.g., about the central longitudinal axis A), relative to the remainder of the body 110, e.g., the transition portion 132 and the main portion 130. In such embodiments, the tab 118 can move between the first position and the second position by rotating about the central longitudinal axis A (i.e., to change the container 115 from the closed state to the open state by fracturing the frangible connection(s) 125). In such embodiments, the applicator 100 can be referred to as a "twist-to-activate" or "twist-off" applicator 100. Such twisting can be accomplished manually by grasping the tab 118 (e.g., by feeling for the tab 118 through the absorbent member 105) and twisting. In some embodiments, the applicator 100 can still be positioned in a sterile package or pouch when the tab 118 is grasped and twisted.

Press-to-activate applicators of the present disclosure can employ tensile/bending stress to fracture the frangible connection(s) 125, whereas twist-to-activate applicators can employ shear stress to fracture the frangible connection(s) 125. In some embodiments, the material of the body 110 can be configured such that in twist-to-activate applicators, fracturing the frangible connection(s) 125 in shear mode requires the tab 118 (and the absorbent member 105 coupled thereto) to rotate less than 135 degrees about the longitudinal direction D, such that the absorbent member 105 does not decouple from the body 110 during rotation. In some embodiments, the tab 118 (and the absorbent member 105 coupled thereto) can rotate less than 120 degrees about the longitudinal direction D; in some embodiments, less than 100 degrees; in some embodiments, less than 90 degrees; in some embodiments, less than 60 degrees; and in some embodiments, less than 45 degrees. In some embodiments, the tab 118 can rotate between 45 degrees and 90 degrees (inclusive) to cause the frangible connection(s) 125 to fracture. In some embodiments, the tab 118 can rotate between 35 degrees and 45 degrees (inclusive) to cause the frangible connection(s) 125 to fracture.

In some embodiments, it can be desirable for the applied force necessary to fracture the frangible connection(s) 125 (i.e., the "activation force," which can be a twisting force, a bending force, or a combination thereof) to be no greater than about 5 lb (about 22 N); in some embodiments, no greater than about 3 lb (about 13 N); in some embodiments, no greater than about 2 lb (about 9 N); and in some embodiments, no greater than about 1 lb (about 4 N). In some embodiments, the activation force ranges from about 0.25 lb (about 1 N) to about 5 lb (about 22 N).

In some embodiments, the body 110, or a portion thereof, such as the container 115, can be substantially transparent, such that the liquid composition is visible inside the container 115 from outside the body 110. However, in some embodiments, the body 110, or a portion thereof, can be substantially non-transparent.

The body 110 can be formed of a variety of materials, including, but not limited to, high-density polyethylene (HDPE), polypropylene (PP), other suitable polymeric materials, or a combination thereof. Particular utility has been found when the body 110 is formed of high-density polyethylene (HDPE), and particularly, a butene copolymer HDPE. One example of a suitable butene copolymer HDPE (available under the trade designation SCLAIR® 56B4 Blow Molding Resin from Nova Chemicals Corporation, Canada) has the material properties specified in Table 1, as measured by the ASTM test method specified in Table 1.

TABLE 1

Material properties of Butene Copolymer HDPE (available under the trade designation SCLAIR ® 56B4 Blow Molding Resin from Nova Chemicals Corporation, Canada)

| Property | ASTM | Value |
| --- | --- | --- |
| Melt Index (at 190 °C./2.16 kg) | D 1238 | 0.34 g/10 min |
| Density | D 792 | 0.947 g/cm$^3$ |
| Yield Strength (at tensile pull speed of 50 mm/min.) | D 638 | 23 MPa |
| Elongation (at tensile pull speed of 50 mm/min.) | D 638 | 675% |
| Flexural Modulus | D 790 | 970 MPa |

An appropriate body material provides an adequate barrier (e.g., to volatile liquid compositions 126) at the nominal wall thickness of the container 115 (and particularly, of the main portion 130 of the container 115; see ranges for wall thickness discussed below), while still allowing the main portion 130 wall to be deformed (e.g., squeezed) without excessive pressure during use. The wall thickness of the container 115 and the frangible connection(s) 125 can be controlled to provide the necessary balance of material properties at the distal end 114 of the body 110 and in the main portion 130. If the wall thickness of the body 110 becomes too thin and weak, it can kink during activation and/or application of the liquid composition 126. However, if the wall of the main portion 130 is too thick, it becomes difficult to pump during use. The present inventors discovered that HDPE at the target wall thickness ranges provides the necessary balance of rigidity at the distal end 114, barrier properties for the container 115, and flexibility at the proximal end 112 (e.g., in the main portion 130).

Density of the material making up the body 110 can be important to ensure that the container 115 (and particularly, the main portion 130 of the container 115) has adequate barrier properties, particularly in embodiments in which the liquid composition 126 comprises a volatile solvent. In some embodiments, the density of the body material can be at least about 0.9 g/cm$^3$; in some embodiments, at least about 0.92 g/cm$^3$; and in some embodiments, at least about 0.94 g/cm$^3$. In some embodiments, the density of the body material can be no greater than about 1 g/cm$^3$; and in some embodiments, no greater than about 0.95 g/cm$^3$. In some embodiments, the density of the body material can be about 0.947 g/cm$^3$.

Elongation to break can also be an important property of the body material. In order to rupture the frangible connection(s) 125 under a tensile load during a press-to-activate mode (i.e., in which the bottom side of each frangible connection 125 is stretched), the elongation of the material can be minimized to minimize the amount that each frangible connection 125 would have to stretch in order to fracture. However, if the elongation is too low, the body material may be too brittle and may result in the body 110 cracking when squeezed during use. In some embodiments, the elongation of the body material (e.g., when tested pursuant to ASTM D 638 at a tensile pull speed of 50 mm/min.) can be no greater than about 700%; in some embodiments, no greater than about 675%; in some embodiments, no greater than about 650%; in some embodiments, no greater than about 600%; in some embodiments, no greater than about 550%; and in some embodiments, no greater than about 500%. In some embodiments, the elongation of the body material can be at least about 200%; in some embodiments, at least about 300%; and in some embodiments, at least about 400%. In some embodiments, the elongation under these test conditions can range from about 300% to about 700%. In some embodiments, the elongation of the body material can be about 675%.

In some embodiments, the melt index of the body material (e.g., when tested pursuant to ASTM D 1238 at 190° C./2.16 kg) can be at least about 0.2 g/10 min; and in some embodiments, at least about 0.3 g/10 min. In some embodiments, the melt index of the body material can be no greater than about 3 g/10 min; and in some embodiments, no greater than about 2 g/10 min. In some embodiments, the melt index of the body material can be about 0.34 g/10 min.

In some embodiments, the yield strength of the body material (e.g., when tested pursuant to ASTM D 638 at a tensile pull speed of 50 mm/min.) can be at least about 20 MPa; and in some embodiments, at least about 23 MPa. In some embodiments, the yield strength of the body material can be no greater than about 35 MPa; in some embodiments, no greater than about 30 MPa; and in some embodiments, no greater than about 25 MPa. In some embodiments, the melt index of the body material can be about 23 MPa.

In some embodiments, the flexural modulus of the body material (e.g., when tested pursuant to ASTM D 790) can be at least about 900 MPa; and in some embodiments, at least about 950 MPa. In some embodiments, the flexural modulus of the body material can be no greater than about 1500 MPa; in some embodiments, no greater than about 1000 MPa; and in some embodiments, no greater than about 950 MPa. In some embodiments, the flexural modulus of the body material can be about 970 MPa.

The absorbent member 105 can be configured to dispense the liquid composition 126 and include any suitable form, such as a swab, a sponge, a foam. The absorbent member 105 can be formed of any of a variety of materials, including, but not limited to, polyurethane foam. Particular utility has been found when the absorbent member 105 is formed of open cell polyurethane foam, comprising from 70 to 100 pores per inch (ppi; about 28-39 pores per cm). The absorbent member 105 can have a variety of shapes, but particularly utility has been found when the absorbent member 105 includes a substantially triangular cross-sectional shape when taken substantially perpendicularly with respect to the lateral direction T (i.e., to define a profile surface), as shown in FIGS. 1-3. Such a triangular shape allows a user to position his/her hand at an angle of about 45 degrees relative to the surface of interest (e.g., a sterile surface), without requiring any additional manipulation (e.g., flexing or bending) of the body 110. As a result, the shape of the absorbent member 105 can aid in facilitating an ergonomically sound application technique.

In some embodiments, the liquid composition 126 can include one or more volatile components or compounds (e.g., solvents). That is, in some embodiments, the liquid composition 126 can include one or more components that have a boiling temperature of about room temperature. For example, in some embodiments, the liquid composition can include aqueous or hydroalcoholic cleansing lotions, gels, mousses, disinfecting or sterilizing fluids, sanitizing gels, and/or other antimicrobial liquids and other compositions that may include one or more volatile or flammable components such as solvent(s). For example, lower alcohols such as $C_1$-$C_4$ monofunctional alcohols, alkanes, silicon compounds such as hexamethyldisiloxane, cyclic silicones as well as other volatile solvents can be used in liquid compositions 126 contained in applicators of the present disclosure.

By way of further example, in some embodiments, the liquid compositions 126 can include an alcohol, such as isopropyl alcohol (IPA) or ethanol. In some embodiments, the liquid compositions 126 can include at least 50% v/v of the alcohol (e.g., IPA); in some embodiments, at least 60% v/v; and in some embodiments, at least 70% v/v.

In some embodiments, the liquid composition 126 can include an antimicrobial agent. Antimicrobial agents can include, but are not limited to, chlorhexidine gluconate (CHG), iodine, povidone-iodine, alexidine, octinedine, polyhexamethyl biguanide (PHMB), other suitable antimicrobial agents, or a combination thereof. In some embodiments, the liquid composition 126 can include at least about 0.5% v/v of antimicrobial agent; in some embodiments, at least about 1% v/v; in some embodiments, at least about 1.5% v/v; in some embodiments, at least about 2% v/v; in some embodiments, at least about 3% v/v; and in some embodiments, at least about 4% v/v.

As shown in FIGS. 1-3, the main portion 130 can include a distal end 142. In some embodiments, the main portion 130 can be elongated along the longitudinal direction D. In some embodiments, as shown in FIGS. 1-7C, the distal end 142 of the main portion 130 can include a substantially vertical surface that can provide, or function as, a longitudinal stop (or support surface) for the absorbent member 105 (e.g., when coupling the absorbent member 105 to the body 110).

In some embodiments, the absorbent member 105 can be dimensioned to receive all of the components of the body 110 located distally with respect to the distal end 142 of the main portion 130, and the components of the body 110 located distally with respect to the distal end 142 of the main portion 130 can be configured to be received in the recess 107 of the absorbent member 105.

In some embodiments, the distal end 142 of the main portion 130 is not oriented at an angle of 90 degrees with respect to the longitudinal direction D and the central longitudinal axis A. The distal end 142 can include a vertical top portion (i.e., half) that extends vertically above the vertical center of the main portion 130 and a vertical bottom portion (i.e., half) that extends vertically below the vertical center of the main portion 130. In some embodiments, each vertical portion of the distal end 142 of the main portion 130 can be oriented at an angle ranging from 60 to 90 degrees with respect to the longitudinal direction D, and particularly, with respect to a horizontal plane comprising the central longitudinal axis A.

The main portion 130 can be configured to house a majority of the liquid composition 126 and can also be configured to be handled and manually manipulated (e.g., squeezed), such that the liquid composition 126 can be pumped from the reservoir 120 using manual pressure.

In some embodiments, as shown in FIGS. 1-7C, the main portion 130 can have an oval cross-sectional shape when taken substantially perpendicularly with respect to the longitudinal direction D (i.e., to define a vertical surface), such that the main portion 130 is longer in the vertical direction V than in the lateral direction T (i.e., has a greater vertical dimension than lateral dimension). For example, the main portion 130 can have a first diameter in the vertical direction V that is greater than a second diameter in the lateral direction T. Such a configuration can facilitate pumping or deforming the main portion 130 of the container 115 to move the liquid composition 126 toward the distal end 124 of the container 115. That is, at least the side portions or sidewalls of the main portion 130 can be deformable. By way of example only, such an oval cross-sectional shape of the main portion 130 can allow the main portion 130 to be held by one hand of a user, with the index finger resting on top of the main portion 130, while the sides of the main portion 130 can be held and/or squeezed between the thumb and one or more remaining fingers (e.g., the index finger).

The oval cross-sectional shape of the main portion 130 can also allow the main portion 130 to be deformed (e.g., squeezed), even if a greater wall thickness of the body 110 is employed, for example, a wall thickness that may be useful for other components of the body 110 (such as the components or elements defining at least a portion of the distal end 114 of the body 110, e.g., the tab 118, the transition portion 132, the one or more ribs 134 and/or at least a portion of the one or more chambers 136) that need to remain rigid in order to impart a sufficient force to the frangible connections in response to an acceptable activation force.

In some embodiments, the wall thickness can also be controlled to provide necessary shelf life stability, particularly in embodiments in which the liquid composition 126 comprises volatile components, as described above. In some embodiments, the wall thickness can also be controlled to provide a suitable fluid (i.e., liquid and vapor) barrier, while allowing at least a portion of the main portion 110 to be deformed. That is, the wall thickness can be controlled to provide walls of the container 115 that provide a sufficient barrier to a volatile liquid composition 126 (i.e., contained in the container 115) and/or to a sterilizing vapor during external sterilization of the device (e.g., ethylene oxide). Furthermore, the wall thickness of the container 115 (and the body 110 as a whole) can be controlled to provide a thin wall in the area of the one or more frangible connections 125 that is weaker than in other areas and is configured to be fractured under a desired activation force.

At least the main portion 130, the transition portion 132, and the one or more ribs 134 can have a uniform, or the same, wall thickness, which can enable making the body 110 with a BFS process. In some embodiments, the wall thickness X (see FIG. 6) of the body 110 can be at least about 0.35 mm; in some embodiments, at least about 0.4 mm; in some embodiments, at least about 0.5 mm; and in some embodiments, at least about 0.6 mm. In some embodiments, the wall thickness X of the body 110 can be no greater than about 1 mm; in some embodiments, no greater than about 0.9 mm; and in some embodiments, no greater than about 0.8 mm. In some embodiments, the wall thickness X is about 0.7 mm (i.e., about 0.028 inches) or 0.8 mm. If the wall thickness X is too thick, the main portion 130 can be too difficult to pump to control the flow of the liquid composition 126; however, if the wall thickness X is too thin, the main portion 130, transition portion 132, or the junction therebetween can kink during activation and/or application.

In some embodiments, as shown in FIGS. 1-3, the main portion 130 of the container 115 can include (e.g., at the proximal end 122 of the container 115) a tapered region (e.g., a circumferential crimp) 131 wherein the main portion 130 has a reduced dimension (e.g., diameter). Such a tapered region 131 can facilitate (and be formed as a result of) sealing the main portion 130 to a blowing nozzle used in a blow-fill-seal (BFS) operation that can inject fluid (e.g., gas and/or the liquid composition 126) during the blowing and/or filling steps. At least partly because of potential heat associated with BFS machinery and processes, in embodiments employing a volatile liquid composition 126, it can be beneficial that the liquid composition 126 be spaced a distance apart from the tapered region 131. For example, when the body 110 is oriented distal-end-down, the liquid composition 126 can be positioned in the reservoir 120 up to a longitudinal liquid level or fill line, and in some embodiments, the fill line can be located a longitudinal distance of at least about 0.5 cm away from (i.e., distally with respect to) the tapered region 131; in some embodiments, at least about 1 cm; in some embodiments, at least about 2 cm; and in some embodiments, at least about 2.5 cm. As mentioned above, this separation between the liquid composition 126 and the tapered region 131 can ensure that high temperature molding parts or machinery do not interact with the liquid composition 126, which can be volatile or flammable, during fabrication.

As shown in FIG. 1, in some embodiments, the applicator 100 can further include an ethylene oxide barrier label 127 coupled to an outer surface of the body 110, for example, by being wrapped around the main portion 130. For simplicity and clarity, the label 127 is shown in FIG. 1 as only covering a portion of the main portion 130; however, in some embodiments, the label 127 can cover the entire main portion 130 (e.g., from the tapered region 131 or the proximal end 112 of the applicator 100 to the distal end 142 of the main portion 130), overlapping as much outer surface area as possible. Examples of suitable barrier labels are described in U.S. Pat. No. 8,105,306, which is incorporated herein by reference. Examples of suitable barrier materials can include, but are not limited to, a metalized aluminum label, a PET label, and combinations thereof. In some embodiments, the barrier label 127 can be formed by co-extruding the barrier label 127 with the material used to make the body 110.

The transition portion 132 is formed adjacent to, and extends distally from, the distal end 142 of the main portion 130 to provide a transition between the main portion 130 and the one or more frangible connections 125. As a result, the transition portion 132 has a cross-sectional area (or average cross-sectional area) that is less than the cross-sectional area (or average cross-sectional area) of the main portion 130. For example, the transition portion 132 can have a width (e.g., a lateral width in the lateral direction T) and/or a height or thickness (e.g., in the vertical direction V) that is less than that of the main portion 130. In the embodiment illustrated in FIGS. 1-7C, the width and the height of the transition portion 132 is less than that of the main portion 130 (see, e.g., FIGS. 2, 3, 5, 6 and 7C). As further shown, in some embodiments, the transition portion 132 can have a lateral width that inhibits the absorbent member 105 from flipping over (i.e., sideways) during use. That is, in some embodiments, the transition portion 132 can have a lateral width that is at least half the lateral width of the main portion 130; in some embodiments, at least two-thirds the lateral width of the main portion 130.

In some embodiments, the transition portion 132 can have a substantially parallelogrammatic (e.g., rectangular) cross-sectional shape, for example, when taken perpendicularly with respect to the longitudinal direction D, the lateral direction T, and/or the vertical direction V. In some embodiments, the transition portion 132 can have a substantially parallelepipedal three-dimensional shape.

In some embodiments, the transition portion 132 can have a lateral width that generally increases distally, such that the transition portion 132 is wider at its distal end 148 (or tip) than it is at its proximal end (or base). Said another way, in some embodiments, the transition portion 132 can have a lateral width that is greatest at its distal end 148. Such an increase in lateral width can be relatively small, e.g., no greater than about a 50% increase; in some embodiments, no greater than about a 40% increase; in some embodiments, no greater than about a 30% increase; in some embodiments, no greater than about a 20% increase; in some embodiments, no greater than about a 15% increase; in some embodiments, no greater that about a 10% increase; and in some embodiments, no greater than about a 5% increase.

The increase in lateral width at the distal end 148 of the transition portion 132 can allow for additional space between adjacent chambers 136, e.g., when a plurality of chambers 136 are employed. This increase in space between adjacent chambers 136 allows for larger chamber dimensions (e.g., diameters) to be employed, which allows for stretching or thinning of the body material during forming to further facilitate creating a "neck down region" of the chambers 136 to form the frangible connections 125, such that the frangible connections 125 are formed of a region of weakened material, relative to the remainder of the body 110 (and the container 115), and the head mold forming die has an adequate thickness.

In some embodiments, the transition portion 132 can have a substantially constant vertical height. In some embodiments, the transition portion 132 has a substantially constant cross-sectional area and shape (e.g., when the cross-section is taken substantially perpendicularly to the longitudinal direction D, the lateral direction T, or the vertical direction V). However, as mentioned above, in some embodiments, the cross-sectional area, e.g., when taken substantially perpendicularly with respect to the longitudinal direction D, may increase distally; however, by "substantially constant," it is meant that the cross-sectional area generally does not decrease distally. In some embodiments, the transition portion 132 can have a substantially constant height (or thickness) in the vertical direction V.

Having a substantial transition portion height gives the applicator 100 strength during activation and when applying the liquid composition 126 to a surface. The strength and rigidity of the transition portion 132 (e.g., resulting from one or more of the geometry (e.g., shape, dimensions, and/or dimensions relative to other elements of the body 110), structure (e.g., combination with the rib 134), material makeup, and wall thickness of the transition portion 132) can be important in both activation and application. In some embodiments, the height (or average height) of the transition portion 132 in the vertical direction V can be at least 25% of the height of the main portion 130; in some embodiments, at least 30%; and in some embodiments, at least 40%. However, the transition portion 130 provides a transition from the main portion 130 dimensions down to the neck down region of the chambers 136 that forms the frangible connections 125. As a result, the height of the transition portion 132 is less than the height of the main portion 130.

The transition portion 132 can also be configured to be coupled to the absorbent member 105, e.g., by being dimensioned to be received in the slot 107 of the absorbent member 105 and/or by providing one or more coupling surfaces for the absorbent member 105, as described below. In addition, the transition portion 132 can be positioned and configured to mechanically support the absorbent member 105, e.g., during fracture of the frangible connection(s) 125 and/or during application of the liquid composition 126 onto a surface (e.g., skin).

Figure 4:
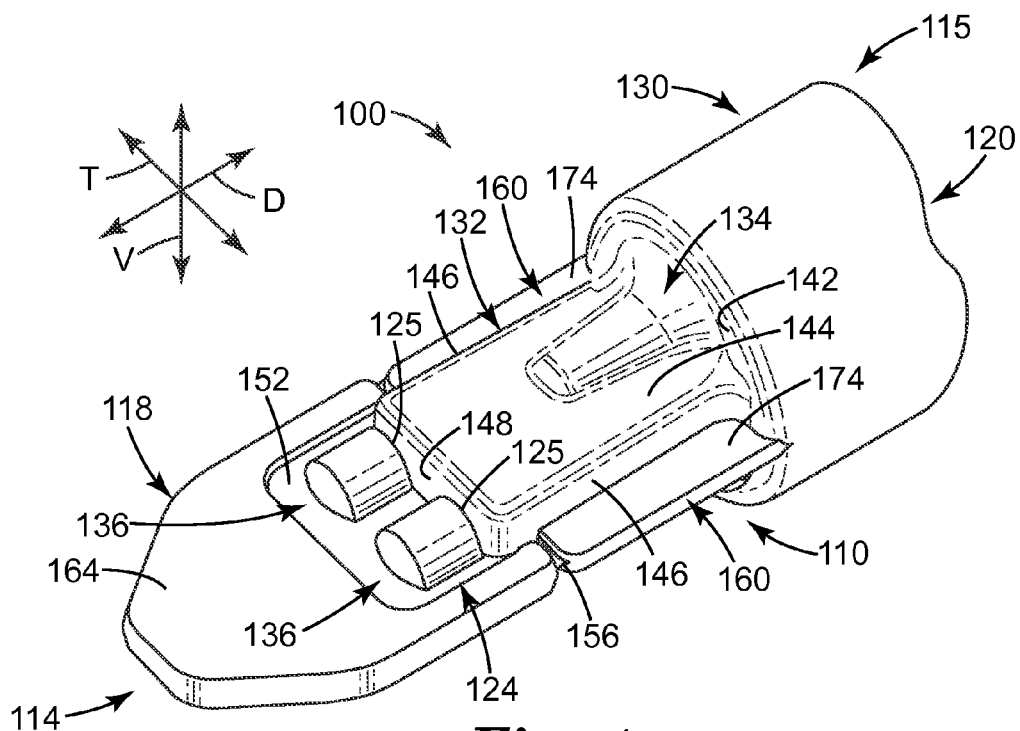
FIG. 4 is a close-up top perspective view of a distal end of the liquid applicator of FIGS. 1-3.

In some embodiments, the transition portion 132 can include at least one substantially planar outer surface that is configured to provide a coupling surface for the absorbent member 105. For example, in some embodiments, the transition portion 132 can include two opposing substantially planar top and bottom surfaces 144, as shown in FIGS. 4-6. In such embodiments, the two opposing substantially planar surfaces 144 can be horizontal surfaces that can be substantially parallel with respect to one another. The absorbent member 105 can be coupled to the surface(s) 144 by any of the above-described coupling means. Having one or more substantially planar surfaces (e.g., horizontal planar surfaces) can be particularly beneficial for providing a coupling surface for the absorbent member 105.

In some embodiments, the substantially planar surface(s) 144 of the transition portion 132 can be oriented at a non-zero angle with respect to the distal end 142 of the main portion 130. For example, in embodiments in which the distal end 142 of the main portion 130 of the container 115 includes a vertical surface, and the surfaces 144 are horizontal surfaces, the surfaces 144 can be oriented substantially perpendicularly with respect to the vertical surface of the distal end 142 of the main portion 130.

As further shown in FIGS. 1-7C, in some embodiments, the transition portion 132 can include other substantially planar surfaces, in addition to the surfaces 144. For example, in some embodiments, the transition portion 132 can include one or more profile surfaces 146 (two substantially opposing profile surfaces 146 are shown by way of example). The profile surfaces 146 can also be used for coupling the absorbent member 105 and the body 110 together.

In some embodiments, the distal end 148 of the transition portion 132 can be radiused adjacent the top and bottom surfaces 144, which can allow the chamber(s) 136 to move (e.g., twist or pivot) freely in a direction needed to cause a fracture at the respective frangible connection(s) 125. In such embodiments, the exact angle of the radiused distal end of the transition portion and/or the chamber geometry is not important, as long as there is clearance for the chamber 136 to move relative to the distal end of the transition portion 132 as needed. In other embodiments, the distal end of the transition portion 132 can be configured (i.e., shaped and dimensioned) to provide a surface or edge, e.g., that is relatively sharp, for the chamber(s) 136 to use as leverage to fracture (e.g., tear) the respective frangible connection(s) 125.

The rib(s) 134 can be referred to as longitudinal rib(s). Because the applicator 100 and body 110 of the embodiment of FIGS. 1-7C has vertical symmetry about a horizontal plane that passes through a vertical center of the applicator 100 (and the body 110), the applicator 100 includes two ribs 134—a top rib 134 and a bottom rib 134. Because of the vertical symmetry of the embodiment of FIGS. 1-7C, the top and bottom ribs 134 are illustrated as being identical. The vertical symmetry can be advantageous, such that there is no prescribed top or bottom to the applicator 100 and either of the illustrated top or bottom of the body 110 can be oriented downwardly during activation (e.g., in a press-to-activate configuration) and/or application. However, it should be noted that the top and bottom ribs 134 need not be identical, and in some embodiments, one of the top and bottom ribs 134 can be longer, wider, taller and/or shaped differently than the other rib 134.

For simplicity, one rib 134 will be described in greater detail, but it should be understood that the same description applies equally to the any other ribs 134 employed. It should be further understood that while two ribs 134 are shown in the embodiment of FIGS. 1-7C, fewer or more than two ribs 134 can be employed in applicators of the present disclosure.

As mentioned above, the rib 134 can also form a portion of the container 115 and extend longitudinally adjacent the transition portion 132 from the distal end 142 of the main portion 130 to a location along the longitudinal length L of the transition portion 132. Specifically, the rib 134 can extend longitudinally adjacent one of the substantially planar surfaces 144 of the transition portion 132.

The rib 134 is integrally formed with both the transition portion 132 and the main portion 130 of the container 115, and is used to support the transition portion 132 during both activation and application of the liquid composition 126 to a surface. As shown in FIGS. 3 and 6, the rib 134 can have a vertical height that extends vertically (e.g., up or down, depending on which rib 134 is being described) from an outer surface of the transition portion 132, and particularly, from one of the substantially planar surfaces 144 of the transition portion 132.

However, in some embodiments, as shown, the rib 134 has a vertical height (or thickness) that is less than that of the transition portion 132 (and the main portion 130). In some embodiments, the rib 134 has a height that extends from a substantially planar (e.g., top) surface 144 of the transition portion 132 to a vertical position that is less than (or within) the vertical height of the main portion 130, and particularly, below the vertical height of the distal end 142 of the main portion 130 (see FIG. 6).

In some embodiments, as shown in FIG. 6, the rib 134 can taper vertically toward the central longitudinal axis A. Said another way, in some embodiments, the vertical dimension (i.e., height or thickness) of the rib 134 can taper (i.e., decrease) distally, such that the greatest (i.e., tallest or thickness) portion of the rib 134 is located at its most proximal location adjacent the distal end 142 of the main portion 130, and the smallest (i.e., shortest or thinnest) portion of the rib 134 is located at its most distal end, at a longitudinal location along the length L of the transition portion 132. That is, in some embodiments, the rib 134 can taper from its proximal end (e.g., adjacent the distal end 142 of the main portion 130) to its distal end (e.g., located at a longitudinal position along the length L of the transition portion 132) in the vertical direction V.

The rib 134 can provide a connection, or bridge, between a substantially planar surface 144, i.e., a substantially horizontal surface, of the transition portion 132 to a surface of the main portion 130, e.g., the substantially vertical surface of the distal end 142 of the main portion 130. The connection provided by the rib 134 can function to add vertical height and strength to the transition portion 132 adjacent the main portion 130, e.g., in a region aligned with the central longitudinal axis A. This additional height and strength provided by the rib 134 can inhibit bending, deforming or kinking the body 110 at the junction between the transition portion 132 and the main portion 130 during activation and/or application, e.g., while maintaining the uniform wall thickness. In addition, this added strength to a portion of the transition portion 132 can ensure that an imparted activation force is directed to, or concentrated at, the frangible connection(s) 125, rather than the junction between the transition portion 132 and the main portion 130, or another location along the length L of the transition portion 132. That is, the rib 134 can concentrate or move the forces (e.g., bending forces, in a press-to-activate configuration) to the longitudinal location of the frangible connection(s) 125, i.e., between the distal end 148 of the transition portion 132 and the chamber(s) 136. The tab 118 can also contribute to concentrating forces (e.g., bending forces) at the longitudinal location of the frangible connection(s) 125.

In some embodiments, the longitudinal length $L_R$ of the rib 134 can be at least half the length L of the transition portion 132, as measured from the distal end 142 of the main portion 130 (see FIG. 5). In some embodiments, the length $L_R$ of the rib 134 can be at least 0.25 times the length L of the transition portion 132, in some embodiments, at least 0.5 times the length L of the transition portion 132, and in some embodiments, at least 0.75 times. In some embodiments, the length $L_R$ of the rib 134 can be less than the length L of the transition portion 132.

In some embodiments, the longitudinal length $L_T$ that the tab 118 extends distally with respect to the transition portion 132 (as measured from the distal end 148 of the transition portion 132) can be at least half the length L of the transition portion 132 (see FIG. 5). In some embodiments, the length $L_T$ of the rib 118 can be at least 0.6 times the length L of the transition portion 132; in some embodiments, at least 0.75 times; in some embodiments, at least 0.9 times; in some embodiments, at least 1 times; in some embodiments, at least 1.25 times; and in some embodiments, at least 1.5 times.

In some embodiments, the rib 134 can have a lateral width that is less than that of the transition portion 132 (and the main portion 130) along its length. Such a configuration can keep more areas of the substantially planar surface 144 of the transition portion 132 and/or the vertical surface of the distal end 142 of the main portion 130 exposed and available, e.g., for coupling with the absorbent member 105. In addition, as mentioned above, if more area of the vertical surface of the distal end 142 of the main portion 130 is exposed, this surface can provide a longitudinal stop for the absorbent member 105.

In some embodiments, as shown in FIG. 5, the rib 134 can taper laterally toward the central longitudinal axis A. Said another way, in some embodiments, the lateral dimension (i.e., width) of the rib 134 can taper (i.e., decrease) distally, such that the greatest (i.e., widest) portion of the rib 134 is located at its most proximal location adjacent the distal end 142 of the main portion 130, and the smallest (i.e., narrowest) portion of the rib 134 is located at its most distal end, at a longitudinal location along the length L of the transition portion 132. That is, in some embodiments, the rib 134 can taper from its proximal end (e.g., adjacent the distal end 142 of the main portion 130) to its distal end (e.g., located at a longitudinal position along the length L of the transition portion 132) in the lateral direction T.

As shown in FIG. 5, in some embodiments, the rib 134 can be laterally centered with respect to the transition portion 132 and/or the main portion 130. In some embodiments, the rib 134 and/or the transition portion 132 can be laterally centered about the central longitudinal axis A. In some embodiments, the rib 134 and/or the transition portion 132 can have lateral symmetry about the central longitudinal axis A (i.e., can be laterally centered with respect to the body 110).

As mentioned above, the embodiment of FIGS. 1-7C has lateral symmetry and includes two off-center (or "off-axis") chambers 136. While the applicators of the present disclosure can include as few as one and as many as structurally necessary or possible, two chambers 136 are illustrated by way of example only.

When a single chamber 136 is employed (see FIG. 9, described below), the chamber 136 can be laterally centered with respect to the remainder of the container 115 and the body 110, i.e., aligned with the central longitudinal axis A. When an even number of multiple chambers 136 are employed, the multiple chambers 136 can be located in off-center (e.g., symmetrical) positions with respect to the central longitudinal axis A. When an odd number of multiple chambers 136 are employed, one of the chambers 136 can be aligned with the central longitudinal axis A, and the other chambers 136 can be located in off-center (e.g., symmetrical) positions.

In some embodiments, employing multiple chambers 136 can allow for multiple, smaller-diameter channels (and accordingly, apertures 138) connecting the chambers 136 to the transition portion 132, which can provide better flow control of the liquid composition 126, such that the main portion 130 would need to be squeezed to pump the liquid composition 126 out of the apertures 138.

As shown, in some embodiments, the tab 118 can include the chambers 136, and the tab 118 can include a recessed portion, area or region 152 in which the chambers 136 are formed. The recessed portion 152 is not hollow (see FIG. 6) and surrounds the chambers 136. When multiple chambers 136 are provided, the tab 118 (e.g., the recessed portion 152) can provide a physical connection between the chambers 136 to facilitate moving the chambers 136 together, relative to the remainder of the container 115 during activation, and to facilitate simultaneous (or substantially simultaneous) fracture of the frangible connections 125. As shown in FIG. 5, the tab 118, and particularly, the recessed portion 152 that connects the two chambers 136, traverses the central longitudinal axis A.

As shown, chambers 136 have a vertical height that is almost as large as that of the transition portion 132, and is greater than the remainder of the tab 118. In some embodiments, the remainder of the tab 118 can be vertically centered with respect to the chambers 136, such that the chambers 136 protrude vertically above and below the remainder of the tab 118 (see FIG. 6).

For simplicity, one chamber 136 and one corresponding frangible connection 125 will be described in greater detail, but it should be understood that the same description applies equally to any other chambers 136 employed.

As mentioned above, the chamber 136 can be coupled to the remainder of the container 115, and particularly, can be coupled to the transition portion 132, and more particularly, can be coupled to the distal end 148 of the transition portion 132, via the frangible connection 125. As a result, when the frangible connection 125 is intact, the container 115 is in its closed state, and the reservoir 120 is not in fluid communication with ambience (or the absorbent member 105), and when the frangible connection 125 is fractured, the container 115 is in its open state, and the reservoir 120 is in fluid communication with ambience (and the absorbent member 105, when the absorbent member 105 and the body 110 are coupled together) via one of the apertures 138 (see FIG. 7C).

The chamber 136 can include a "neck-down" region, as shown in FIGS. 5 and 6, where the chamber 136 tapers laterally and vertically in a proximal direction, i.e., toward the distal end 148 of the transition portion 132.

In some embodiments, as shown in the embodiment of FIGS. 1-7C, the chamber 136 can have an oval cross-sectional shape when taken substantially perpendicularly with respect to the longitudinal direction D (i.e., to define a vertical surface), such that the chamber 136 is longer in the vertical direction V than in the lateral direction T (i.e., has a greater vertical dimension than lateral dimension). For example, the chamber 136 can have a first diameter in the vertical direction V that is greater than a second diameter in the lateral direction T. Such a configuration can facilitate fitting more chambers 136 along the distal end 148 of the transition portion 132, while still providing sufficient necking down to provide sufficiently weakened frangible connections 125 at their desired locations. However, it should be understood that other cross-sectional shapes are possible and within the spirit and scope of the present disclosure, as described below with respect to FIGS. 8 and 9.

The tab 118 will now be described in greater detail. The tab 118 does not form a portion of the container 115, such that the tab 118 is not in fluid communication with the reservoir 120, or the elements making up the container 115. In some embodiments, as shown in FIG. 6, at least a portion of the tab 118 can be hollow and can include a second reservoir 140; however, the second reservoir 140 is not in fluid communication with the reservoir 120 of the container 115. In some embodiments employing the second reservoir 140, the second reservoir 140 can be a means for making the tab 118 thicker (or taller, i.e., in the vertical direction V) and stronger to facilitate activation. However, even in such embodiments, the body 110 can still be formed by BFS, because the wall thickness of the tab 118 is still the same, even though the overall thickness (or height, i.e., in the vertical direction V) of the tab 118 may be larger. In some embodiments, if the main portion 130, the transition portion 132, and the rib 134 have a uniform wall thickness of X, the wall thickness of the tab 118 can also be X, while the overall thickness of the tab 118 can be about 3X.

As described above, the tab 118 can have a sufficient length and thickness to apply sufficient activation force to fracture the frangible connection(s) 125. In addition, the tab 118 can be of sufficient length and width to provide support to the absorbent member 105 during application of the liquid composition (e.g., to skin). However, in some embodiments, the tab 118 completely severs from the remainder of the body 110 during activation and may not provide much support to the absorbent member 105 during application.

The tab 118 (or a distal end thereof) can be configured to engage a surface (e.g., a hard surface) in press-to-activate configurations or can be configured to be grasped and twisted in twist-to-activate configurations. As mentioned above, the tab 118 can be configured to be received within the recess 107 of the absorbent member 105. The tab 118 can also be configured to be coupled to the absorbent member 105, e.g., by providing one or more substantially planar surfaces 164, as shown in FIGS. 4-6, to which the absorbent member 105 can be coupled. In some embodiments, the substantially planar surface(s) 164 can be oriented substantially similarly as the substantially planar surface(s) 144 of the transition portion 132. By way of example, the tab 118 includes two substantially planar surfaces 164 that are substantially horizontal surfaces—i.e., a top surface and a bottom surface—both of which can be coupled to the absorbent member 118. In addition, the tab 118 can provide a sufficient lateral width to inhibit the absorbent member 105 from flipping over (e.g., side-to-side) during application. In general, the tab 118 is wider than the total, overall lateral width of the one or more chambers 136 (and any space(s) therebetween). In some embodiments, the lateral width of the tab 118 can be at least half the width of the main portion 130, in some embodiments, at least two-thirds the width of the main portion 130, and in some embodiments, can have a lateral width substantially the same as that of the main portion 130, such that the lateral or side edges of the tab 118 are collinear with the lateral sides of the main portion 130.

The tab 118 primarily extends longitudinally distally and slightly laterally with respect to the transition portion 132. However, in some embodiments, as shown in FIGS. 4-6, the tab 118 can include at least one proximal extension (or projection, or flange, or overhang) 154 that extends proximally adjacent the transition portion 132 (e.g., a lateral side thereof) along a portion of the length L of the transition portion 132. Because of the lateral symmetry of the applicator 100, the tab 118 of the applicator 100 includes two proximal extensions 154, by way of example.

As shown, the proximal extensions 154 can extend proximally with respect to the distal end 148 of the transition portion 132. The proximal extensions 154 can provide a proximal overhang of the tab 118, which can inhibit unintentional or premature fracturing of the frangible connection(s) 125, e.g., during assembly of the absorbent member 105 onto the body 110). However, the proximal extensions 154 do not extend so far proximally that they would move the bending plane (i.e., in press-to-activate configurations) away from (e.g., proximally with respect to) the distal end 148 of the transition portion 132, or the location of the frangible connection(s) 125.

In some embodiments, the length of the proximal extensions 154 is relatively short, such that the proximal end of the proximal extensions 154 is as close to the longitudinal position of the frangible connections 125 as possible. In some embodiments, each proximal extension of the tab 118 can be separated from other portions of the body 110, and particularly, from a lateral rib 160 (described in greater detail below) by a minimal distance, such that a relatively small longitudinal gap exists between the proximal extensions 154 and the lateral ribs 160. In some embodiments, the tab 118 does not include any proximal extensions.

In some embodiments, each proximal extension 154 of the tab 118 extends along, or overhangs, the transition portion 132 by a longitudinal length (i.e., as measured proximally from the distal end 148 of the transition portion 132) that is less than one-third the length L of the transition portion 132; in some embodiments, less than one quarter the length L; in some embodiments, less than 0.2 times the length L; and in some embodiments, less than 0.1 times the length L.

As mentioned above, the tab 118 is coupled to the transition portion 132, and particularly, the distal end 148 of the transition portion 132, via the frangible connection(s) 125. However, the tab 118 is also coupled (e.g., frangibly) to the transition portion 132 via a web or flash 156 of minimally thin body material that extends around the distal end 148 of the transition portion 132, between the chambers 136 when more than one is employed, between the proximal extension(s) 154 and the transition portion 132, and/or in a gap between the proximal extension 154 and a lateral rib 160. That is, the web 156 can be positioned to couple at least a portion of the transition portion 132 and the tab 118, such that the transition portion 132 and the tab 118 are coupled together via the web 156 when the container 115 is in the closed state, and there are no gaps or openings between the transition portion 132 and the tab 118. The web 156 can be formed during the blow-fill-seal (BFS) operation, and can function to help secure the chambers 136 to inhibit accidental rupture when inserting the distal end 114 of the body 110 into the absorbent member 105 during assembly. In some embodiments, only a minimal amount of web 156 is employed, as too much web 156 (i.e., too vertically thick) can shift the bending plane (i.e., in press-to-activate embodiments) toward the proximal end 112 of the body 110, away from the desired location. In some embodiments, at least a portion of the web 156, along with the frangible connection(s) 125, can be fractured during activation.

As mentioned above, in some embodiments, the body 110 can further include one or more lateral ribs 160 formed adjacent one or more lateral sides of the transition portion 132 and extending longitudinally adjacent at least a portion of the length L of the transition portion 132. While the rib(s) 134 are hollow and form a portion of the container 115, the lateral rib(s) 160 do not form portion of the container 115 and are not in fluid communication with the reservoir 120. Because of the lateral symmetry of the applicator 100, the applicator 100 is illustrated as including two lateral ribs 160 by way of example. For simplicity, one lateral rib 160 will be described in greater detail, but it should be understood that the same description applies equally to any other lateral ribs 160 employed.

The lateral rib 160 is positioned and configured to add structural rigidity to the transition portion 132. Because the lateral rib 160 is not hollow, and because the body 110 (or at least all of the body 110 except the chambers 136 and the frangible connections 125) has the same nominal wall thickness that can be formed by BFS, when the two sides come together to form the lateral rib 160, the overall thickness (or height, i.e., in the vertical direction V) of the lateral rib 160 can be about 2X, if the uniform wall thickness is X. As a result, in some embodiments, as shown in FIG. 3, the hollow portion of the tab 118 comprising the second reservoir 140 can have a vertical dimension (i.e., 3X) that is greater than that of the lateral rib 160 (i.e., 2X). The recessed portion 152 (i.e., the non-hollow portion) of the tab 118, however, can have the same overall thickness as that of the lateral rib 160, i.e., 2X.

In some embodiments, the lateral rib 160 can be vertically centered with respect to the transition portion 132 (and the main portion 130, as well as the body 110 as a whole). The lateral rib 160 can extend substantially longitudinally along a lateral side of the transition portion 132, such that the lateral rib 160 is parallel with the longitudinal direction D and the central longitudinal axis A. In some embodiments, as shown in FIG. 5, the lateral rib 160 can have a length $L_L$ that is at least one-half the length L of the transition portion 132; and in some embodiments, at least 0.75 or three-quarters the length L of the transition portion 132.

The lateral rib 160 is integrally formed with and coextensive with at least a portion of the lateral side of the transition portion 132, such that the lateral rib 160 forms a lateral extension of the transition portion 132. The lateral rib 160 can also be thought of as forming a longitudinal extension of the main portion 130, and the outermost lateral side or edge of the lateral rib 160 can be collinear with the lateral side or edge of the main portion 130. In some embodiments, the lateral width of the lateral rib 160 can be at least one quarter the width of the transition portion 132 (or the average width of the transition portion 132, or the maximum width of the transition portion 132); in some embodiments, the width of the lateral rib 160 can be at least one-third the width of the transition portion 132. In some embodiments, the lateral rib 160 can have a lateral width that is no greater than one-half the width of the transition portion 132 (or the average width of the transition portion 132, or the maximum width of the transition portion 132). In general, the lateral width of the transition portion 132 can be determined, and then the lateral width of the lateral rib 160 can be whatever dimension is necessary to laterally extend from the lateral side of the transition portion 132 to a lateral position that is collinear with the lateral side of the main portion 130.

In some embodiments, the lateral rib 160 can include one or more substantially planar surfaces 174, e.g., substantially horizontal surfaces (see FIGS. 3-5). Because of the vertical symmetry of the applicator 100, the lateral rib 160 can include top and bottom substantially horizontal surfaces 174. The substantially planar surfaces 174 can provide additional coupling surfaces for coupling the absorbent member 105 and the body 110 together.

FIGS. 7A-7C illustrate a method of using the applicator 100 of FIGS. 1-6, and particularly, show a press-to-activate method of activating the applicator 100.

As shown in FIG. 7A, activation of the applicator 100 in a press-to-activate method can include bringing the tab 118 into contact with a surface (e.g., a hard surface) S, which can cause a portion (e.g., a bottom) of the absorbent member 105 to be compressed between the body 110 (e.g., the tab 118) and the surface S. During activation, the applicator 100, and particularly, the central longitudinal axis A of the applicator 100, can be angled with respect to the surface S at an activation start angle α. The activation start angle α is the angle the applicator 100 is positioned with respect to the surface S, not the angle that the tab 118 needs to move relative to the central longitudinal axis A to cause fracture.

In some embodiments, the activation start angle α can be at least about 10 degrees with respect to the surface S; in some embodiments, at least about 20 degrees; in some embodiments, at least about 30 degrees; and in some embodiments, at least about 45 degrees. In some embodiments, the activation start angle α can be no greater than about 80 degrees with respect to the surface S; in some embodiments, no greater than 75 degrees; in some embodiments, no greater than 70 degrees; in some embodiments, no greater than 60 degrees; and in some embodiments, no greater than 50 degrees. In some embodiments, the activation start angle α can be about 45 degrees.

As is evident in FIGS. 7A-7B, press-to-activate activation puts the frangible connection 125 under bending stress, such that the bottom of the frangible connection(s) 125 is subjected to tensile stress. The ribs 134, the tab 118, the lateral ribs 160, and the relative sizing of the elements of the distal end 114 of the body 110 add sufficient rigidity and strength to the distal end 114 of the body 110 to inhibit bending or kinking between the main portion 130 and the transition portion 132 and to ensure that the stresses are concentrated at the frangible connection(s) 125. This can be true, even while ensuring the main portion 130 remains sufficiently deformable for pumping the liquid composition 126 out of the reservoir 120.

As shown in FIGS. 7A and 7B, pressing the tab 118 into the surface S causes the tab 118 to pivot about the transverse axis B (see FIG. 5) and out of alignment with the central longitudinal axis A. The tab 118 also pivots with respect to the transition portion 132 and the main portion 130, and this activation force is imparted to the one or more frangible connections 125, where the body wall is necked down or thinned to form a weakened region.

As shown in FIGS. 7B and 7C, after the frangible connection(s) 125 have fractured (i.e., after the channels formed by the frangible connection(s) 125 that couple the chamber(s) 136 to the remainder of the container 115 have fractured), the apertures 138 are formed in the body 110, and particularly, in the distal end 148 of the transition portion 132. When the frangible connection(s) 125 have fractured, the container 115 has changed from its closed state (see FIGS. 1-7A) to its open state (see FIGS. 7B and 7C). When the container 115 is in the open state, the transition portion 132 (and the reservoir 120) are in fluid communication with ambience and the absorbent member 105. The tab 118 and the absorbent member 105 are removed from FIG. 7C for clarity.

As further shown in FIG. 7B, the frangible connection(s) 125 are not fractured until it is desired to change the container 115 from its open state to its closed state. That is, following the fracture of the frangible connection(s) 125, the reservoir 120 of the container 115 is positioned in direct fluid communication with the absorbent member 105 via the apertures 138, and the liquid composition 126 does not need to flow through any other compartments or elements of the applicator 100.

As shown in FIG. 7B, in some embodiments, the tab 118 can be completely separated from the remainder of the body 110 after the frangible connection(s) 125 are fractured. However, the tab 118 can remain within the absorbent member 105. After fracture, the substantially planar surfaces 144 and 174 of the transition portion 132 and the lateral rib 160, respectively, can be particularly useful in continuing to support the absorbent member 105 during application of the liquid composition 126. However, in some embodiments, at least a portion of the tab 118 can remain coupled to the remainder of the body 110 after the frangible connection(s) 125 have fractured. For example, this can occur in twist-to-activate embodiments when two or more off-axis chambers 136 are employed, and only one frangible connection 125 is completely fractured from the twist.

The apertures 138 can be sized to inhibit the liquid composition 126 in the reservoir 120 from freely running or dripping out of the reservoir 120 as soon as the apertures 138 are formed. That is, the apertures 138 can be sized to inhibit the liquid composition 126 from dripping out of the apertures 138 until the main portion 130 is squeezed to pump the liquid composition 126 out of the reservoir 120. This can be particularly useful, e.g., in embodiments employing a volatile or flammable liquid composition 126, such that a flammable liquid does not begin uncontrollably pooling out over the skin surface of a patient. On the other hand, the apertures 138 can be sized to allow the liquid composition 126 to be pumped out of the reservoir 120 with a reasonable squeezing force to cause the liquid composition 126 to flow out of the container 115 when desired.

In some embodiments, the number of apertures 138 employed can also be controlled to inhibit the liquid composition 126 from freely spilling out of the apertures 138. In some embodiments, employing multiple chambers 136 can provide for multiple, smaller apertures 138 after activation, as opposed to employing a single chamber 136 having a single frangible connection 125 that forms a single aperture 138. However, even in embodiments employing a single chamber 136, the resulting aperture 138 can be sized to provide flow control of the liquid composition 126. In addition, in some embodiments, the container 115 can include a single (e.g., enlarged) chamber 136 that includes more than one frangible connection 125 to the transition portion 132, such that the size and/or number of apertures 138 can still be controlled even when only one chamber 136 is employed.

In some embodiments, the patient's skin surface may not be sufficiently hard or rigid to provide a suitable surface for fracturing the frangible connection(s) 125 in a press-to-activate activation method. As a result, in some embodiments, the surface S is a sterile hard surface that is not the skin surface to which the liquid composition 126 will be applied. In some embodiments, the surface S is not sterile, and the applicator 100 is activated in a sterile package or pouch.

An exemplary method of making the applicator 100 will now be described. As mentioned above, a blow-fill-seal (BFS) operation can be employed to make the body 110. In some embodiments, the BFS method can include providing a mold comprising a negative of a desired outer shape of the body 110. Such a mold can include a pair of mating mold halves, and can include a negative of at least a portion of the body 110, such as the distal end 114 (e.g., at least a portion of the tab 118, the chamber 136, the transition portion 132, the rib 134, and/or at least a portion of the main portion 130 of the container 115) and including the closed distal end 124 of the container 115. Next, the method can include providing a heated parison of a polymeric material from which the body 110 will be formed. The heated parison can be enclosed in the mold (e.g., between two or more mating mold sections).

A gas can be injected into the parison in order to effect blow molding of the polymeric material to form at least a portion of the body 110 having an open proximal end. Subsequently and/or simultaneously, negative pressure can be applied to the outside of at least a portion of the parison in to form at least the distal end 114 of the body 110, including, e.g., the transition portion 132, the rib 134, the chamber 136, and the tab 118. The still open-ended body 110 can then be filled (e.g., sterile filled) with the liquid composition 126. Blowing and/or filling can be accomplished by sealing the still open proximal end of the body 110 to a blowing and/or filling nozzle. Finally, the still open proximal end of the body 110 (i.e., of the container 115) can be sealed to form the single-piece, unitary body that comprises the container 115 with a closed distal end 124 and a closed proximal end 122, and the liquid composition 126 positioned in the reservoir 120 of the container 115 (i.e., that is closed from ambience).

The method of making the applicator 100 can further include coupling the absorbent member 105 to at least a portion of the body 110 (e.g., the distal end 114) by any of the above-described coupling means. For example, the absorbent member 105 can be coupled to at least one or more of the tab 118, the transition portion 132, the lateral ribs 160, and the distal end 142 of the main portion 130.

Figure 8:
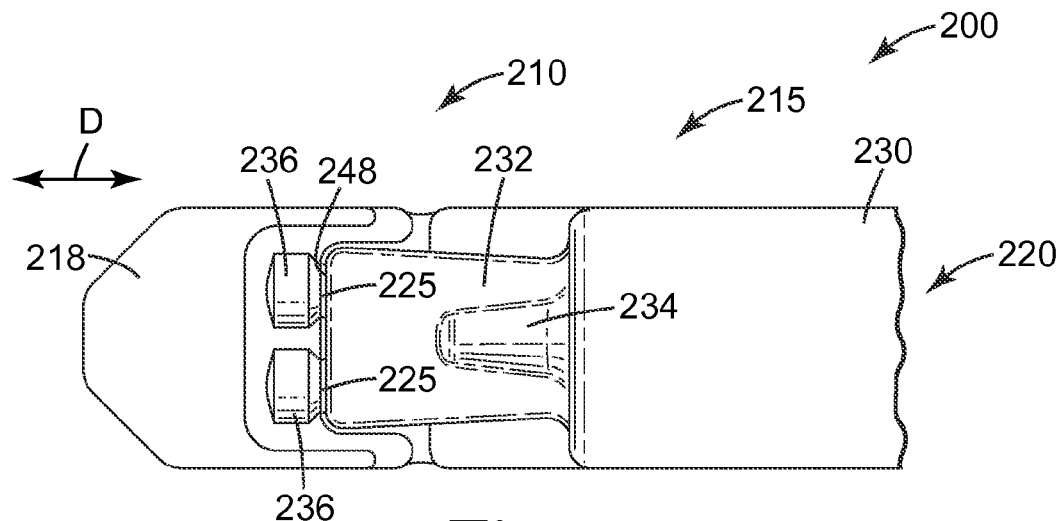
FIG. 8 is a close-up top plan view of a distal end of a liquid applicator according to another embodiment of the present disclosure.

Additional exemplary embodiments of liquid applicators of the present disclosure will now be described with respect to FIGS. 8-9. FIGS. 8-6 illustrate various applicators of the present disclosure, wherein like numerals represent like elements. The applicators of FIGS. 8-9 share many of the same elements, features, and functions as the applicator 100 described above with respect to FIGS. 1-7C. Reference is made to the description above accompanying FIGS. 1-7C for a more complete description of the features and elements (and alternatives to such features and elements) of the embodiments illustrated in FIGS. 8-9. Any of the features described above with respect to FIGS. 1-7C can be applied to the embodiments of FIGS. 8-9, and vice versa.

FIG. 8 illustrates a liquid applicator 200 according to another embodiment of the present disclosure. The liquid applicator 200 includes a single-piece, unitary, integral body 210. The applicator 200 can also include an absorbent member, such as the absorbent member 105 described above, but the absorbent member is removed from FIG. 8 for simplicity and clarity.

The body 210 can include a container 215 that defines a reservoir 220, and a tab 218. The container 215 can include or be defined by at least a main portion 230, a transition portion 232, one or more ribs 234, and one or more chambers 236 (two are shown by way of example in the embodiment illustrated in FIG. 8).

The applicator 200 is substantially the same as the applicator 100 of FIGS. 1-7C, except that the two chambers 236 of the applicator 200 have a substantially round (i.e., circular) cross-sectional shape when taken substantially perpendicularly with respect to a longitudinal direction D (i.e., to define a vertical surface), such that the chamber 236 has the same dimension (i.e., diameter) in all directions. As shown, a distal end 248 of the transition portion 232 can be sized (e.g., by having a lateral width that is appropriately sized) to accommodate multiple round chambers 236, while still ensuring sufficient stretching or thinning of the body material in the neck-down region of the chambers 236 to create a frangible connection 225 adjacent each chamber 236.

Similar to the applicator 100 of FIGS. 1-7C, the applicator 200 can be activated in a press-to-activate configuration or a twist-to-activate configuration.

Figure 9:
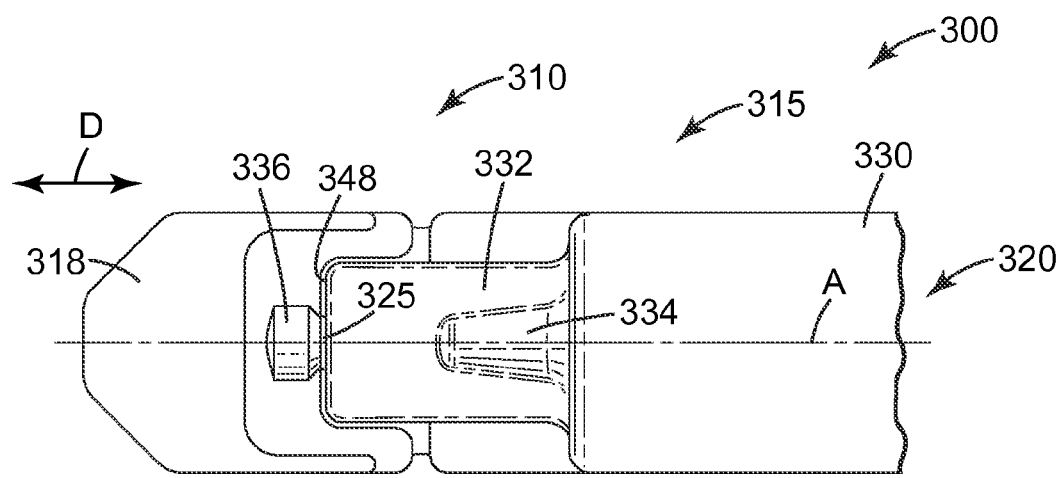
FIG. 9 is a close-up top plan view of a distal end of a liquid applicator according to another embodiment of the present disclosure.

FIG. 9 illustrates a liquid applicator 300 according to another embodiment of the present disclosure. The liquid applicator 300 includes a single-piece, unitary, integral body 310. The applicator 300 can also include an absorbent member, such as the absorbent member 105 described above, but the absorbent member is removed from FIG. 9 for simplicity and clarity.

The body 310 can include a container 315 that defines a reservoir 320, and a tab 318. The container 315 can include or be defined by at least a main portion 330, a transition portion 332, one or more ribs 334, and one or more chambers 336 (one is shown by way of example in the embodiment illustrated in FIG. 9).

The applicator 300 is substantially the same as the applicator 100 of FIGS. 1-7C, except that only a single chambers 336 is employed in the applicator 300, and the single chamber 336 has a substantially round (i.e., circular) cross-sectional shape when taken substantially perpendicularly with respect to a longitudinal direction D (i.e., to define a vertical surface), such that the single chamber 336 has the same dimension (i.e., diameter) in all directions. While a distal end 348 of the transition portion 332 is shown as being of the same dimensions as that of the applicator 100 of FIGS. 1-7C and the applicator 200 of FIG. 8, it should be understood that in embodiments employing single chamber 336, the distal end 348 of the transition portion 332 need not be wider than its proximal end.

As mentioned above, in some embodiments employing a single chamber 336, the chamber 336 can be laterally centered with respect to the remainder of the container 115 and the body 110, i.e., aligned with a central longitudinal axis A.

In addition, while a round-cross-sectional chamber 336 is shown in FIG. 9, it should be understood that any other suitable cross-sectional shape can be employed in the single-chamber applicator 300, without departing from the spirit and scope of the present disclosure.

Similar to the applicator 100 of FIGS. 1-7C and the applicator 200 of FIG. 8, the applicator 300 can be activated in a press-to-activate configuration or a twist-to-activate configuration, and can be particularly suitable for twist-to-activate activations.

Each embodiment shown in the figures is illustrated as a separate embodiment for clarity in illustrating a variety of features of the applicators of the present disclosure.

However, it should be understood that any combination of elements and features of any of the embodiments illustrated in the figures and described herein can be employed in the applicators of the present disclosure.

The following embodiments are intended to be illustrative of the present disclosure and not limiting.

Embodiments

Embodiment 1 is a liquid applicator comprising:
an absorbent member configured to dispense a liquid composition; and
a single-piece, unitary body having a central longitudinal axis that defines a longitudinal direction, the body having a lateral direction oriented substantially perpendicularly with respect to the longitudinal direction and a vertical direction oriented substantially perpendicularly with respect to the longitudinal direction and the lateral direction, the body configured to be coupled to the absorbent member and providing at least one coupling surface for the absorbent member, the body comprising:
a closed container defining a reservoir, wherein the liquid composition is positioned in at least a portion of the reservoir, wherein the container includes a closed proximal end and a closed distal end and is configured to be changed from a closed state in which the reservoir is not in fluid communication with ambience to an open state in which the reservoir is in fluid communication with ambience, the container further comprising:
a main portion defining the closed proximal end of the container and including a distal end,
a transition portion extending distally from the distal end of the main portion, the transition portion having a cross-sectional area less than the cross-sectional area of the main portion, the transition portion having a length in the longitudinal direction, the transition portion configured to be coupled to the absorbent member,
a rib extending longitudinally adjacent the transition portion from the distal end of the main portion to a location along the length of the transition portion, the rib having a vertical height that extends vertically from an outer surface of the transition portion, and
a chamber defining the closed distal end of the container, the chamber coupled to the transition portion via a frangible connection, such that the container is in the closed state when the frangible connection is intact and the container is in the open state and in fluid communication with ambience via an aperture formed in the transition portion when the frangible connection is fractured,
wherein the main portion, the transition portion, the rib, and the chamber each define a portion of the reservoir, and wherein at least the main portion, the transition portion, and the rib have a uniform wall thickness; and
a tab comprising the chamber, the tab coupled to the transition portion at least by the frangible connection, the tab being movable with respect to the transition portion between a first position in which the frangible connection is intact and a second position in which the frangible connection is fractured.

Embodiment 2 is the liquid applicator of embodiment 1, wherein the tab also has the uniform wall thickness.

Embodiment 3 is the liquid applicator of embodiment 1 or 2, wherein the body is formed of a high-density polyethylene.

Embodiment 4 is the liquid applicator of any of embodiments 1-3, wherein the liquid composition comprises a volatile compound.

Embodiment 5 is the liquid applicator of any of embodiments 1-4, wherein the absorbent member includes a recess configured to receive at least the tab, the chamber, the transition portion, and the rib.

Embodiment 6 is the liquid applicator of any of embodiments 1-5, wherein the transition portion includes a substantially planar surface.

Embodiment 7 is the liquid applicator of embodiment 6, wherein the substantially planar surface provides a coupling surface for the absorbent member.

Embodiment 8 is the liquid applicator of embodiment 6 or 7, wherein the substantially planar surface is a substantially horizontal surface.

Embodiment 9 is the liquid applicator of any of embodiments 6-8, wherein the rib extends adjacent the substantially planar surface of the transition portion and the vertical height of the rib extends vertically from the substantially planar surface of the transition portion.

Embodiment 10 is the liquid applicator of any of embodiments 6-9, wherein the distal end of the main portion includes a substantially vertical surface, wherein the substantially planar surface of the transition portion is a substantially horizontal surface oriented substantially perpendicularly with respect to the substantially vertical surface of the main portion of the container, and wherein the rib is positioned to connect the substantially vertical surface of the main portion with the substantially horizontal surface of the transition portion.

Embodiment 11 is the liquid applicator of embodiment 10, wherein the substantially vertical surface of the main portion provides a stop for the absorbent member.

Embodiment 12 is the liquid applicator of any of embodiments 1-11, wherein the transition portion has a substantially parallelogrammatic cross-sectional shape.

Embodiment 13 is the liquid applicator of any of embodiments 1-12, wherein the transition portion has a substantially parallelepipedal shape.

Embodiment 14 is the liquid applicator of any of embodiments 1-13, further comprising a web of material positioned to couple at least a portion of the transition portion and the tab.

Embodiment 15 is the liquid applicator of any of embodiments 1-14, wherein the rib is laterally symmetrical about the central longitudinal axis.

Embodiment 16 is the liquid applicator of any of embodiments 1-15, wherein the rib is laterally centered with respect to the transition portion.

Embodiment 17 is the liquid applicator of any of embodiments 1-16, wherein the rib has a vertical height that tapers distally.

Embodiment 18 is the liquid applicator of any of embodiments 1-17, wherein the rib has a proximal end and a distal end, and wherein the rib tapers from its proximal end to its distal end in the vertical direction.

Embodiment 19 is the liquid applicator of any of embodiments 1-18, wherein rib has a lateral width that tapers distally.

Embodiment 20 is the liquid applicator of any of embodiments 1-19, wherein the rib has a proximal end and a distal end, and wherein the rib tapers from its proximal end to its distal end in a lateral direction.

Embodiment 21 is the liquid applicator of any of embodiments 1-20, wherein the rib has a length in the longitudinal direction that is at least half the length of the transition portion.

Embodiment 22 is the liquid applicator of any of embodiments 1-21, wherein the rib has a length in the longitudinal direction that is less than the length of the transition portion.

Embodiment 23 is the liquid applicator of any of embodiments 1-22, wherein the rib has a length in the longitudinal direction and a lateral width in the lateral direction, and wherein the lateral width of the rib is less than a lateral width of the transition portion along the length of the rib.

Embodiment 24 is the liquid applicator of any of embodiments 1-23, wherein the transition portion has a lateral width, and wherein the lateral width generally increases distally.

Embodiment 25 is the liquid applicator of any of embodiments 1-24, wherein the transition portion has a lateral width that is greatest at a distal end of the transition portion.

Embodiment 26 is the liquid applicator of any of embodiments 1-25, wherein the transition portion has a vertical height that is less than a vertical height of the main portion of the container.

Embodiment 27 is the liquid applicator of any of embodiments 1-26, wherein the transition portion has a substantially constant vertical height.

Embodiment 28 is the liquid applicator of any of embodiments 1-27, wherein the cross-sectional shape of the transition portion is substantially constant.

Embodiment 29 is the liquid applicator of any of embodiments 1-28, wherein the body further comprises a lateral rib formed adjacent a lateral side of the transition portion and extending longitudinally adjacent at least a portion of the length of the transition portion.

Embodiment 30 is the liquid applicator of embodiment 29, wherein the lateral rib has an outer lateral edge that is collinear with an outer lateral surface of the main portion.

Embodiment 31 is the liquid applicator of embodiment 29 or 30, wherein the lateral rib provides a coupling surface for the absorbent member.

Embodiment 32 is the liquid applicator of any of embodiments 29-31, further comprising a web of material positioned to couple at least a portion of the lateral rib and the tab.

Embodiment 33 is the liquid applicator of any of embodiments 29-32, wherein the lateral rib is coextensive with at least a portion of the lateral side of the transition portion.

Embodiment 34 is the liquid applicator of any of embodiments 29-33, wherein the lateral rib is vertically centered with respect to the transition portion.

Embodiment 35 is the liquid applicator of any of embodiments 29-34, wherein the lateral rib is one of two lateral ribs, symmetrically positioned on opposite lateral sides of the transition portion.

Embodiment 36 is the liquid applicator of any of embodiments 29-35, wherein at least a portion of the tab is hollow and defines a second reservoir that is not in fluid communication with the reservoir of the container, wherein at least the hollow portion of the tab has a vertical height that is greater than a vertical height of the lateral rib.

Embodiment 37 is the liquid applicator of any of embodiments 1-36, wherein at least a portion of the tab is hollow and defines a second reservoir that is not in fluid communication with the reservoir of the container.

Embodiment 38 is the liquid applicator of embodiment 37, wherein the tab includes a recessed portion that is not hollow adjacent the chamber.

Embodiment 39 is the liquid applicator of any of embodiments 1-38, wherein the distal end of the main portion of the container is positioned to function as a stop for the absorbent member.

Embodiment 40 is the liquid applicator of any of embodiments 1-39, wherein the chamber protrudes vertically from the tab, such that the chamber has a vertical height that is greater than a vertical height of the remainder of the tab.

Embodiment 41 is the liquid applicator of any of embodiments 1-40, wherein the chamber laterally and vertically tapers in a proximal direction, toward a distal end of the transition portion to form the frangible connection.

Embodiment 42 is the liquid applicator of any of embodiments 1-41, wherein the tab provides at least one coupling surface for the absorbent member.

Embodiment 43 is the liquid applicator of any of embodiments 1-42, wherein the tab is dimensioned to be received in the absorbent member.

Embodiment 44 is the liquid applicator of any of embodiments 1-43, wherein the tab is not in fluid communication with the container.

Embodiment 45 is the liquid applicator of any of embodiments 1-44, wherein the tab has a length in the longitudinal direction, and wherein the length of the tab is at least half the length of the transition portion.

Embodiment 46 is the liquid applicator of any of embodiments 1-45, wherein the transition portion is in direct fluid communication with the absorbent member via the aperture when the frangible connection is fractured and the absorbent member is coupled to the body.

Embodiment 47 is the liquid applicator of any of embodiments 1-46, wherein the tab is pivotally movable with respect to the transition portion between the first position and the second position about a transverse axis oriented substantially perpendicularly with respect to the central longitudinal axis.

Embodiment 48 is the liquid applicator of embodiment 47, wherein the tab is configured to engage a hard surface to cause the tab to pivotally move with respect to the transition portion about the transverse axis.

Embodiment 49 is the liquid applicator of any of embodiments 1-48, wherein the tab is rotatable with respect to the transition portion about the longitudinal axis between the first position and the second position.

Embodiment 50 is the liquid applicator of any of embodiments 1-49, wherein the tab includes a proximal extension that extends at least partially longitudinally and proximally with respect to the transition portion.

Embodiment 51 is the liquid applicator of embodiment 50, wherein the proximal extension has a length in the longitudinal direction, measured from a distal end of the transition portion, that is no greater than ⅓ of the length of the transition portion. Embodiment 52 is the liquid applicator of any of embodiments 1-51, wherein the transition portion is dimensioned to be received within a recess in the absorbent member.

Embodiment 53 is the liquid applicator of any of embodiments 1-52, wherein the main portion has an oval cross-sectional shape.

Embodiment 54 is the liquid applicator of any of embodiments 1-53, wherein the main portion of the container has a vertical dimension and a lateral dimension, and wherein the vertical dimension is greater than the lateral dimension.

Embodiment 55 is the liquid applicator of any of embodiments 1-54, wherein the chamber is centrally located with respect to the central longitudinal axis.

Embodiment 56 is the liquid applicator of any of embodiments 1-55, wherein the chamber is one of a plurality of chambers and the frangible connection is one of a plurality of frangible connections, wherein the plurality of chambers are coupled together by the tab, such that the plurality of frangible connections are configured to fracture together.

Embodiment 57 is the liquid applicator of embodiment 56, wherein each of the plurality of chambers is located off-center with respect to the central longitudinal axis. Embodiment 58 is the liquid applicator of any of embodiments 1-57, wherein the aperture is dimensioned to inhibit movement of the liquid composition through the aperture until sufficient pressure is applied to the liquid composition in the container.

Embodiment 59 is the liquid applicator of any of embodiments 1-58, wherein the chamber has a vertical dimension and a lateral dimension, and wherein the vertical dimension is greater than the lateral dimension.

Embodiment 60 is the liquid applicator of any of embodiments 1-59, wherein the chamber has an oval cross-sectional shape.

Embodiment 61 is the liquid applicator of any of embodiments 1-60, wherein the liquid composition is sterile.

Embodiment 62 is the liquid applicator of any of embodiments 1-61, wherein the liquid composition comprises an antimicrobial agent.

Embodiment 63 is the liquid applicator of embodiment 62, wherein the antimicrobial agents includes at least one of chlorhexidine gluconate (CHG), iodine, povidone-iodine, alexidine, octinedine, polyhexamethyl biguanide (PHMB), and a combination thereof.

Embodiment 64 is the liquid applicator of any of embodiments 1-63, further comprising an ethylene-oxide barrier label coupled to an outer surface of the body.

Embodiment 65 is the liquid applicator of any of embodiments 1-64, wherein the single-piece, unitary body is formed by a blow-fill-seal (BFS) process.

Embodiment 66 is a method of making the single-piece, unitary body of any of the preceding embodiments, the method comprising a blow-fill-seal (BFS) process.

Embodiment 67 is a method of making the single-piece, unitary body of any of the preceding embodiments, the method comprising:
  providing a mold comprising a negative of a desired outer shape of the single-piece, unitary body, wherein the mold includes a negative of at least a portion of the body including the closed distal end of the container;
  providing a heated parison of a polymeric material;
  enclosing the heated parison in the mold;
  injecting a gas into the parison in order to effect blow molding of the polymeric material to form at least a portion of the body having an open proximal end;
  applying a negative pressure to the outside of at least a portion of the parison in to form the transition portion, the rib, the chamber, and the tab;
  filling the body with the liquid composition; and
  sealing the open proximal end of the body to form the single-piece, unitary body that comprises the container with a closed distal end and a closed proximal end, and the liquid composition positioned in the reservoir of the container.

Embodiment 68 is a method of making a liquid applicator, the method comprising:
  providing the single-piece, unitary body formed according to the method of embodiment 67; and
  coupling an absorbent member to at least one of the tab and the transition portion of the body.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:
1. A liquid applicator comprising:
  an absorbent member configured to dispense a liquid composition; and
  a single-piece, unitary body having a central longitudinal axis that defines a longitudinal direction, the body having a lateral direction oriented substantially perpendicularly with respect to the longitudinal direction and a vertical direction oriented substantially perpendicularly with respect to the longitudinal direction and the lateral direction, the body configured to be coupled to the absorbent member and providing at least one coupling surface for the absorbent member, the body comprising:

a closed container defining a reservoir, wherein the liquid composition is positioned in at least a portion of the reservoir, wherein the container includes a closed proximal end and a closed distal end and is configured to be changed from a closed state in which the reservoir is not in fluid communication with ambience to an open state in which the reservoir is in fluid communication with ambience, the container further comprising:
a main portion defining the closed proximal end of the container and including a distal end,
a rectangular transition portion extending distally from the distal end of the main portion, the transition portion having a cross-sectional area less than the cross-sectional area of the main portion, the transition portion having a length in the longitudinal direction, the transition portion configured to be coupled to the absorbent member, the transition portion having planar top and bottom surfaces,
a rib extending longitudinally adjacent the transition portion from the distal end of the main portion to a location along the length of the transition portion, the rib having a vertical height that extends vertically from an outer surface of the transition portion, and
a chamber defining the closed distal end of the container, the chamber coupled to the transition portion via a frangible connection, such that the container is in the closed state when the frangible connection is intact and the container is in the open state and in fluid communication with ambience via an aperture formed in the transition portion when the frangible connection is fractured, wherein the main portion, the transition portion, the rib, and the chamber each define a portion of the reservoir, and wherein at least the main portion, the transition portion, and the rib have a uniform wall thickness; and
a tab comprising the chamber, the tab coupled to the transition portion at least by the frangible connection, the tab being movable with respect to the transition portion between a first position in which the frangible connection is intact and a second position in which the frangible connection is fractured.

2. The liquid applicator of claim 1, wherein the main portion has an oval cross-sectional shape.

3. The liquid applicator of claim 1, wherein the chamber has an oval cross-sectional shape.

4. The liquid applicator of claim 1, wherein the liquid composition comprises a volatile compound.

5. The liquid applicator of claim 1, wherein the planar top and bottom surfaces provide a coupling surface for the absorbent member.

6. The liquid applicator of claim 1, wherein the planar top and bottom surfaces are substantially horizontal.

7. The liquid applicator of claim 1, wherein the rib extends adjacent the planar top and bottom surfaces of the transition portion and the vertical height of the rib extends vertically from the planar top and bottom surfaces of the transition portion.

8. The liquid applicator of claim 1, wherein the distal end of the main portion includes a substantially vertical surface, wherein the planar top and bottom surfaces of the transition portion is a substantially horizontal surface oriented substantially perpendicularly with respect to the substantially vertical surface of the main portion of the container, and wherein the rib is positioned to connect the substantially vertical surface of the main portion with the substantially horizontal surface of the transition portion.

9. The liquid applicator of claim 1, wherein the distal end of the main portion includes a substantially vertical surface, and wherein the substantially vertical surface of the main portion provides a stop for the absorbent member.

10. The liquid applicator of claim 1, wherein the rib has a length in the longitudinal direction that is at least half the length of the transition portion.

11. The liquid applicator of claim 1, wherein the rib has a length in the longitudinal direction and a lateral width in the lateral direction, and wherein the lateral width of the rib is less than a lateral width of the transition portion along the length of the rib.

12. The liquid applicator of claim 1, wherein the transition portion has a lateral width, and wherein the lateral width generally increases distally.

13. The liquid applicator of claim 1, wherein the transition portion has a substantially constant vertical height.

14. The liquid applicator of claim 1, wherein the body further comprises a lateral rib formed adjacent a lateral side of the transition portion and extending longitudinally adjacent at least a portion of the length of the transition portion.

15. The liquid applicator of claim 1, wherein the tab is pivotally movable with respect to the transition portion between the first position and the second position about a transverse axis oriented substantially perpendicularly with respect to the central longitudinal axis.

16. The liquid applicator of claim 1, wherein the tab is rotatable with respect to the transition portion about the longitudinal axis between the first position and the second position.

17. The liquid applicator of claim 1, wherein the chamber is one of a plurality of chambers and the frangible connection is one of a plurality of frangible connections, wherein the plurality of chambers are coupled together by the tab, such that the plurality of frangible connections are configured to fracture together.

18. The liquid applicator of claim 1, further comprising an ethylene-oxide barrier label coupled to an outer surface of the body.

* * * * *